United States Patent
Chaudhary et al.

(10) Patent No.: US 9,622,913 B2
(45) Date of Patent: Apr. 18, 2017

(54) IMAGING-CONTROLLED LASER SURGICAL SYSTEM

(75) Inventors: Gautam Chaudhary, Laguna Hills, CA (US); Peter Goldstein, Santa Ana, CA (US); Imre Hegedus, Budapest (HU); Carlos German Suárez, Tustin, CA (US); David Calligori, Rancho Santa Margarita, CA (US); Michael Karavitis, Dana Point, CA (US)

(73) Assignee: Alcon LenSx, Inc., Aliso Viejo, CA (US)

( * ) Notice: Subject to any disclaimer, the term of this patent is extended or adjusted under 35 U.S.C. 154(b) by 159 days.

(21) Appl. No.: 13/110,352

(22) Filed: May 18, 2011

(65) Prior Publication Data

US 2012/0296319 A1    Nov. 22, 2012

(51) Int. Cl.
| | | |
|---|---|---|
| *A61F 9/008* | (2006.01) | |
| *A61B 3/14* | (2006.01) | |
| *A61B 18/00* | (2006.01) | |

(52) U.S. Cl.
CPC ...... *A61F 9/00825* (2013.01); *A61B 2018/00636* (2013.01); *A61F 2009/0087* (2013.01); *A61F 2009/00844* (2013.01); *A61F 2009/00889* (2013.01)

(58) Field of Classification Search
CPC ............. A61F 2009/0087; A61F 9/008; A61F 2009/00851; A61F 2009/00889; A61F 9/00825; A61F 2009/00844; A61B 2018/00636
USPC .......................................... 128/898; 606/4–6
See application file for complete search history.

(56) References Cited

U.S. PATENT DOCUMENTS

| | | |
|---|---|---|
| 4,164,222 A | 8/1979 | Prokhorov et al. |
| 4,198,143 A | 4/1980 | Karasawa |
| 4,235,529 A | 11/1980 | Kawase et al. |
| 4,465,348 A | 8/1984 | Lang |
| 4,520,816 A | 6/1985 | Schachar et al. |
| 4,533,222 A | 8/1985 | Ishikawa |
| 4,538,608 A | 9/1985 | L'Esperance, Jr. |
| 4,554,917 A | 11/1985 | Tagnon |

(Continued)

FOREIGN PATENT DOCUMENTS

| | | |
|---|---|---|
| EP | 1444946 | 8/2004 |
| WO | 98/08048 | 2/1998 |

(Continued)

OTHER PUBLICATIONS

Arimoto et al., "Imaging Properties of Axicon in a Scanning Optical System," Nov. 1, 1992, Applied Optics, 31 (31):6652-6657.

(Continued)

*Primary Examiner* — Gary Jackson
*Assistant Examiner* — Scott T Luan
(74) *Attorney, Agent, or Firm* — S. Brannon Latimer

(57) ABSTRACT

An imaging-based laser system can include a laser-beam system, configured to generate and scan a beam of laser pulses with an adjustable laser-power parameter to points of a scan-pattern in an eye, and an imaging-based laser-controller, configured to image a layer in the eye, to control the scanning of the beam of laser pulses to the points of the scan-pattern, and to control a laser-power parameter of the laser pulses according to the distance of the points of the scan-pattern from the imaged layer.

29 Claims, 26 Drawing Sheets

(56) References Cited

U.S. PATENT DOCUMENTS

| | | |
|---|---|---|
| 4,638,801 A | 1/1987 | Daly et al. |
| 4,764,005 A | 8/1988 | Webb et al. |
| 4,881,808 A | 11/1989 | Bille et al. |
| 4,901,718 A | 2/1990 | Bille et al. |
| 4,907,586 A | 3/1990 | Bille et al. |
| 5,048,946 A | 9/1991 | Sklar et al. |
| 5,049,147 A | 9/1991 | Danon |
| 5,054,907 A | 10/1991 | Sklar et al. |
| 5,098,426 A | 3/1992 | Sklar et al. |
| 5,112,328 A | 5/1992 | Taboada et al. |
| 5,139,022 A | 8/1992 | Lempert |
| 5,246,435 A | 9/1993 | Bille et al. |
| 5,255,025 A | 10/1993 | Volk |
| 5,286,964 A | 2/1994 | Fountain |
| 5,321,501 A | 6/1994 | Swanson et al. |
| 5,336,215 A | 8/1994 | Hsueh et al. |
| 5,391,165 A | 2/1995 | Fountain et al. |
| 5,439,462 A | 8/1995 | Bille et al. |
| 5,493,109 A | 2/1996 | Wei et al. |
| 5,549,632 A | 8/1996 | Lai |
| 5,656,186 A | 8/1997 | Mouron et al. |
| 5,738,676 A | 4/1998 | Hammer et al. |
| 5,779,696 A | 7/1998 | Berry et al. |
| 5,795,295 A | 8/1998 | Hellmuth et al. |
| 5,936,706 A | 8/1999 | Takagi |
| 5,954,648 A | 9/1999 | Van Der Brug |
| 5,954,711 A | 9/1999 | Ozaki et al. |
| 5,994,690 A | 11/1999 | Kulkarni et al. |
| 6,004,314 A | 12/1999 | Wei et al. |
| 6,095,648 A | 8/2000 | Birngruber et al. |
| 6,099,522 A | 8/2000 | Knopp et al. |
| 6,137,585 A | 10/2000 | Hitzenberger et al. |
| 6,254,595 B1 | 7/2001 | Juhasz et al. |
| 6,288,784 B1 | 9/2001 | Hitzenberger et al. |
| 6,314,311 B1 | 11/2001 | Williams et al. |
| 6,317,616 B1 | 11/2001 | Glossop |
| 6,337,925 B1 | 1/2002 | Cohen et al. |
| 6,377,349 B1 | 4/2002 | Fercher |
| 6,379,005 B1 | 4/2002 | Williams et al. |
| 6,451,009 B1 | 9/2002 | Dasilva et al. |
| 6,454,761 B1 | 9/2002 | Freedman |
| 6,497,701 B2 | 12/2002 | Shimmick et al. |
| 6,529,758 B2 | 3/2003 | Shahidi |
| 6,579,282 B2 | 6/2003 | Bille et al. |
| 6,623,476 B2 | 9/2003 | Juhasz et al. |
| 6,687,010 B1 | 2/2004 | Horii et al. |
| 6,730,074 B2 | 5/2004 | Bille et al. |
| 6,741,359 B2 | 5/2004 | Wei et al. |
| 6,751,033 B2 | 6/2004 | Goldstein et al. |
| 6,755,819 B1 | 6/2004 | Waelti |
| 6,763,259 B1 | 7/2004 | Hauger et al. |
| 6,769,769 B2 | 8/2004 | Podoleanu et al. |
| 6,775,007 B2 | 8/2004 | Izatt et al. |
| 6,863,667 B2 | 3/2005 | Webb et al. |
| 6,887,232 B2 | 5/2005 | Bille |
| 6,899,707 B2 | 5/2005 | Scholler et al. |
| 6,932,807 B1 | 8/2005 | Tomita et al. |
| 6,991,629 B1 | 1/2006 | Juhasz et al. |
| 7,006,232 B2 | 2/2006 | Rollins et al. |
| 7,018,376 B2 | 3/2006 | Webb et al. |
| 7,027,233 B2 | 4/2006 | Goldstein et al. |
| 7,061,622 B2 | 6/2006 | Rollins et al. |
| 7,072,045 B2 | 7/2006 | Chen et al. |
| 7,072,047 B2 | 7/2006 | Westphal et al. |
| 7,079,254 B2 | 7/2006 | Kane et al. |
| 7,102,756 B2 | 9/2006 | Izatt et al. |
| 7,113,818 B2 | 9/2006 | Podoleanu et al. |
| 7,126,693 B2 | 10/2006 | Everett et al. |
| 7,130,054 B2 | 10/2006 | Ostrovsky et al. |
| 7,133,137 B2 | 11/2006 | Shimmick |
| 7,139,077 B2 | 11/2006 | Podoleanu et al. |
| 7,145,661 B2 | 12/2006 | Hitzenberger |
| 7,148,970 B2 | 12/2006 | de Boer |
| 7,184,148 B2 | 2/2007 | Alphonse |
| 7,207,983 B2 | 4/2007 | Hahn et al. |
| 7,248,371 B2 | 7/2007 | Chan et al. |
| 7,268,885 B2 | 9/2007 | Chan et al. |
| 7,280,221 B2 | 10/2007 | Wei |
| 7,307,733 B2 | 12/2007 | Chan et al. |
| 7,310,150 B2 | 12/2007 | Guillermo et al. |
| 7,312,876 B2 | 12/2007 | Chan et al. |
| 7,319,566 B2 | 1/2008 | Prince et al. |
| 7,329,002 B2 | 2/2008 | Nakanishi |
| 7,330,270 B2 | 2/2008 | O'Hara et al. |
| 7,330,273 B2 | 2/2008 | Podoleanu et al. |
| 7,335,223 B2 | 2/2008 | Obrebski |
| 7,336,366 B2 | 2/2008 | Choma et al. |
| 7,342,659 B2 | 3/2008 | Horn et al. |
| 7,347,548 B2 | 3/2008 | Huang et al. |
| 7,352,444 B1 | 4/2008 | Seams et al. |
| 7,355,716 B2 | 4/2008 | de Boer et al. |
| 7,364,296 B2 | 4/2008 | Miller et al. |
| 7,365,856 B2 | 4/2008 | Everett et al. |
| 7,365,859 B2 | 4/2008 | Yun et al. |
| 7,370,966 B2 | 5/2008 | Fukuma et al. |
| 7,371,230 B2 | 5/2008 | Webb et al. |
| 7,372,578 B2 | 5/2008 | Akiba et al. |
| 7,388,672 B2 | 6/2008 | Zhou et al. |
| 7,390,089 B2 | 6/2008 | Loesel et al. |
| 7,400,410 B2 | 7/2008 | Baker et al. |
| 7,402,159 B2 | 7/2008 | Loesel et al. |
| 7,426,037 B2 | 9/2008 | Ostrovsky et al. |
| 7,433,046 B2 | 10/2008 | Everett et al. |
| 7,452,077 B2 | 11/2008 | Meyer et al. |
| 7,452,080 B2 | 11/2008 | Wiltberger et al. |
| 7,461,658 B2 | 12/2008 | Jones et al. |
| 7,466,423 B2 | 12/2008 | Podoleanu et al. |
| 7,470,025 B2 | 12/2008 | Iwanaga |
| 7,477,764 B2 | 1/2009 | Haisch |
| 7,480,058 B2 | 1/2009 | Zhao et al. |
| 7,480,059 B2 | 1/2009 | Zhou et al. |
| 7,488,070 B2 | 2/2009 | Hauger et al. |
| 7,488,930 B2 | 2/2009 | Ajgaonkar et al. |
| 7,492,466 B2 | 2/2009 | Chan et al. |
| 7,503,916 B2 | 3/2009 | Shimmick |
| 7,508,525 B2 | 3/2009 | Zhou et al. |
| 7,535,577 B2 | 5/2009 | Podoleanu et al. |
| 7,537,591 B2 | 5/2009 | Feige et al. |
| 7,557,928 B2 | 7/2009 | Ueno |
| 7,575,322 B2 | 8/2009 | Somani |
| 7,593,559 B2 | 9/2009 | Toth et al. |
| 7,602,500 B2 | 10/2009 | Izatt et al. |
| 7,604,351 B2 | 10/2009 | Fukuma et al. |
| 7,614,744 B2 | 11/2009 | Abe |
| 7,630,083 B2 | 12/2009 | de Boer et al. |
| 7,631,970 B2 | 12/2009 | Wei |
| 7,633,627 B2 | 12/2009 | Choma et al. |
| 7,643,152 B2 | 1/2010 | de Boer et al. |
| 7,797,119 B2 | 9/2010 | De Boer et al. |
| 7,813,644 B2 | 10/2010 | Chen et al. |
| 7,898,712 B2 | 3/2011 | Adams et al. |
| 8,262,646 B2 | 9/2012 | Frey et al. |
| 8,382,745 B2 * | 2/2013 | Naranjo-Tackman et al. ... 606/5 |
| 8,394,084 B2 * | 3/2013 | Palankar et al. ............... 606/6 |
| 2001/0022648 A1 | 9/2001 | Lai |
| 2002/0013574 A1 | 1/2002 | Elbrecht et al. |
| 2002/0082466 A1 | 6/2002 | Han |
| 2002/0097374 A1 | 7/2002 | Payne et al. |
| 2002/0133145 A1 | 9/2002 | Gerlach et al. |
| 2002/0198516 A1 | 12/2002 | Knopp |
| 2003/0090674 A1 | 5/2003 | Zeylikovich et al. |
| 2003/0206272 A1 | 11/2003 | Cornsweet et al. |
| 2004/0039378 A1 | 2/2004 | Lin |
| 2004/0059321 A1 | 3/2004 | Knopp et al. |
| 2004/0151466 A1 | 8/2004 | Crossman-Bosworth et al. |
| 2004/0243233 A1 | 12/2004 | Phillips |
| 2005/0010109 A1 | 1/2005 | Faul |
| 2005/0015120 A1 | 1/2005 | Seibel et al. |
| 2005/0021011 A1 | 1/2005 | LaHaye |
| 2005/0173817 A1 | 8/2005 | Fauver et al. |
| 2005/0192562 A1 | 9/2005 | Loesel et al. |
| 2005/0201633 A1 | 9/2005 | Moon et al. |
| 2005/0203492 A1 | 9/2005 | Nguyen et al. |
| 2005/0215986 A1 | 9/2005 | Chernyak et al. |

(56) References Cited

U.S. PATENT DOCUMENTS

| | | |
|---|---|---|
| 2005/0284774 A1 | 12/2005 | Mordaunt |
| 2005/0286019 A1 | 12/2005 | Wiltberger et al. |
| 2005/0288745 A1 | 12/2005 | Andersen et al. |
| 2006/0020172 A1 | 1/2006 | Luerssen et al. |
| 2006/0077346 A1 | 4/2006 | Matsumoto |
| 2006/0100613 A1 | 5/2006 | McArdle et al. |
| 2006/0179992 A1 | 8/2006 | Kermani |
| 2006/0187462 A1 | 8/2006 | Srinivasan et al. |
| 2006/0195076 A1 | 8/2006 | Blumenkranz et al. |
| 2006/0206102 A1 | 9/2006 | Shimmick |
| 2007/0013867 A1 | 1/2007 | Ichikawa |
| 2007/0121069 A1 | 5/2007 | Andersen et al. |
| 2007/0126985 A1 | 6/2007 | Wiltberger et al. |
| 2007/0129709 A1 | 6/2007 | Andersen et al. |
| 2007/0129775 A1 | 6/2007 | Mordaunt et al. |
| 2007/0147730 A1 | 6/2007 | Wiltberger et al. |
| 2007/0173791 A1 | 7/2007 | Raksi |
| 2007/0173794 A1 | 7/2007 | Frey et al. |
| 2007/0173795 A1 | 7/2007 | Frey et al. |
| 2007/0185475 A1 | 8/2007 | Frey et al. |
| 2007/0189664 A1 | 8/2007 | Andersen et al. |
| 2007/0216909 A1 | 9/2007 | Everett et al. |
| 2007/0219541 A1 | 9/2007 | Kurtz |
| 2007/0230520 A1 | 10/2007 | Mordaunt et al. |
| 2007/0282313 A1 | 12/2007 | Huang et al. |
| 2007/0291277 A1 | 12/2007 | Everett et al. |
| 2007/0299429 A1 | 12/2007 | Amano |
| 2008/0033406 A1 | 2/2008 | Andersen et al. |
| 2008/0049188 A1 | 2/2008 | Wiltberger et al. |
| 2008/0055543 A1 | 3/2008 | Meyer et al. |
| 2008/0056610 A1 | 3/2008 | Kanda |
| 2008/0071254 A1 | 3/2008 | Lummis et al. |
| 2008/0088795 A1 | 4/2008 | Goldstein et al. |
| 2008/0100612 A1 | 5/2008 | Dastmalchi et al. |
| 2008/0281303 A1 | 11/2008 | Culbertson et al. |
| 2008/0281413 A1 | 11/2008 | Culbertson et al. |
| 2008/0319427 A1 | 12/2008 | Palanker |
| 2009/0012507 A1 | 1/2009 | Culbertson et al. |
| 2009/0088734 A1 | 4/2009 | Mordaunt |
| 2009/0125005 A1 | 5/2009 | Chernyak et al. |
| 2009/0131921 A1 | 5/2009 | Kurtz et al. |
| 2009/0149742 A1 | 6/2009 | Kato et al. |
| 2009/0157062 A1 | 6/2009 | Hauger et al. |
| 2009/0161827 A1 | 6/2009 | Gertner et al. |
| 2009/0168017 A1 | 7/2009 | O'Hara et al. |
| 2009/0177189 A1 | 7/2009 | Raksi |
| 2009/0268161 A1 | 10/2009 | Hart et al. |
| 2010/0004641 A1 | 1/2010 | Frey et al. |
| 2010/0004643 A1 | 1/2010 | Frey et al. |
| 2010/0007848 A1 | 1/2010 | Murata |
| 2010/0022994 A1 | 1/2010 | Frey et al. |
| 2010/0022995 A1 | 1/2010 | Frey et al. |
| 2010/0022996 A1 | 1/2010 | Frey et al. |
| 2010/0042079 A1 | 2/2010 | Frey et al. |
| 2010/0110377 A1 | 5/2010 | Maloca et al. |
| 2010/0137850 A1* | 6/2010 | Culbertson et al. ............... 606/6 |
| 2010/0292678 A1* | 11/2010 | Frey et al. ......................... 606/5 |
| 2010/0324543 A1 | 12/2010 | Kurtz et al. |
| 2011/0022036 A1 | 1/2011 | Frey et al. |
| 2011/0106066 A1* | 5/2011 | Bor ..................................... 606/5 |
| 2011/0118609 A1 | 5/2011 | Goldshleger et al. |
| 2011/0166557 A1* | 7/2011 | Naranjo-Tackman et al. ... 606/5 |
| 2011/0184392 A1* | 7/2011 | Culbertson et al. ............... 606/4 |
| 2011/0184395 A1* | 7/2011 | Schuele et al. ................... 606/5 |
| 2011/0196350 A1* | 8/2011 | Friedman et al. ................. 606/6 |
| 2011/0202046 A1* | 8/2011 | Angeley et al. ................... 606/6 |
| 2011/0319873 A1 | 12/2011 | Raksi et al. |
| 2012/0089134 A1* | 4/2012 | Horvath et al. ................... 606/6 |
| 2012/0274903 A1 | 11/2012 | Sayeram et al. |

FOREIGN PATENT DOCUMENTS

| | | |
|---|---|---|
| WO | 03/062802 | 7/2003 |
| WO | 2006074469 | 7/2006 |
| WO | 2007/084694 | 7/2007 |
| WO | 2007106326 | 9/2007 |
| WO | 2007/130411 | 11/2007 |
| WO | 2010/075571 | 7/2010 |
| WO | 2011/011788 | 1/2011 |

OTHER PUBLICATIONS

Birngruber et al., "In-Vivo Imaging of the Development of Linear and Non-Linear Retinal Laser Effects Using Optical Coherence Tomography in Correlation with Histopathological Findings," 1995, Proc. SPIE 2391:21-27.

Chinn, S.R., et al., "Optical coherence tomography using a frequency-tunable optical source", Optics Letters, 22 (5):340-342, Mar. 1997.

European Search Report, European Patent Application No. 10191057.8, mailed Mar. 16, 2011, to be published by the USPTO.

Fercher et al., "Eye-Length Measurement by Interferometry With Partially Coherent Light," Mar. 1988, Optics Letters, 13(3):186-188.

Fercher et al., "Measurement of Intraocular Distances by Backscattering Spectral Interferometry," May 15, 1995, Optics Comm. 117:43-48.

Hee, M., et al., "Femtosecond transillumination optical coherence tomography", Optics Letters, 18(12):950-952, Jun. 1993.

Huber, R., et al., "Three-dimensional and C-mode OCT imaging with a compact, frequency swept laser source at 1300 nm", Optics Express, 13(26):10523-10538, Dec. 2005.

Izatt et al., "Micron-Resolution Biomedical Imaging With Optical Coherence Tomography," Oct. 1993, Optics & Photonics News, pp. 14-19.

Kamensky, V., et al., "In situ monitoring of the middle IR laser ablation of a cataract-suffered human lens by optical coherent tomography", Proc. SPIE, 2930:222-229, 1996.

Kamensky, V., et al., "Monitoring and animation of laser ablation process in cataracted eye lens using coherence tomography", Proc. SPIE, 2981:94-102, 1997.

Massow, O., et al., "Optical coherence tomography controlled femtosecond laser microsurgery system", Proceedings of the SPIE—Optical Coherence Tomography and Coherence Techniques III, vol. 6627, pp. 662717(1)-662717(6), Aug. 2007.

Ohmi, M., et al., "In-situ Observation of Tissue Laser Ablation Using Optical Coherence Tomography", Optical and Quantum Electronics, 37(13-15):1175-1183, Dec. 2005.

Ostaszewski et al., "Risley prism Beam Pointer", Proc. of SPIE, vol. 6304, 630406-1 thru 630406-10.

PCT International Search Report for International Application No. PCT/US2011/023710 mailed Aug. 24, 2011.

PCT International Search Report for International Application No. PCT/US2011/025332 mailed Sep. 16, 2011.

PCT International Search Report for International Application No. PCT/US2010/056701 mailed Jan. 12, 2011.

PCT International Search Report for International Application No. PCT/US2008/075511 mailed Mar. 12, 2009.

Sarunic, M., et al., "Instantaneous complex conjugate resolved spectral domain and swept-source OCT using 3×3 fiber couplers", Optics Express, 13(3):957-967, Feb. 2005.

Sarunic, M., et al., "Real-time quadrature projection complex conjugate resolved Fourier domain optical coherence tomography", Optics Letters, 31(16):2426-2428, Aug. 2006.

Sarunic, M., et al., "Imaging the Ocular Anterior Segment With Real-Time, Full-Range Fourier-Domain Optical Coherence Tomography", Archives of Ophthalmology, 126(4):537-542, Apr. 2008.

Stern et al., "Femtosecond Optical Ranging of Corneal Incision Depth," Jan. 1989, Investigative Ophthalmology & Visual Science, 30(1):99-104.

Swanson et al., "In vivo retinal imaging by optical coherence tomography", Optics Letters, 18(21), 1864-1866, Nov. 1993.

Tao, Y., et al., "High-speed complex conjugate resolved retinal spectral domain optical coherence tomography using sinusoidal phase modulation", Optics letters, 32(20):2918-2920, Oct. 2007.

(56) References Cited

OTHER PUBLICATIONS

Wojtkowski et al., "In Vivo Human Retinal Imaging by Fourier Domain Optical Coherence Tomography," Jul. 2002, Journal of Biomedical Optics 7(3):457-463, 7 pages.
Yun, S.H., et al., "Wavelength-swept fiber laser with frequency shifted feedback and resonantly swept intra-cavity acoustooptic tunable filter", IEEE Journal of Selected Topics in Quantum Electronics, 3(4):1087-1096, Aug. 1997.
PCT International Search Report corresponding to PCT Application Serial No. PCT/US2011/051466 dated Apr. 10, 2012.
Partial International Search Report corresponding to PCT Application Serial No. PCT/US2012/035927 dated Aug. 3, 2012.
PCT International Search Report dated Jun. 29, 2012 for International Application No. PCT/US2011/051360, filed Sep. 13, 2011.
PCT International Search Report and Written Opinion dated Feb. 9, 2012 for International Application Serial No. PCT/US2011/040223.
Aslyo-Vogel et al., "Darstellung von LTK-Läsionen durch optische Kurzkohärenztomographie (OCT) und Polarisationsmikroskopie nach Sirius-Rot-Fäbung", Ophthalmologe, pp. 487-491, 7-97.
Bagayev et al., "Optical coherence tomography for in situ monitoring of laser corneal ablation", Journal of Biomedical Optics, 7(4), pp. 633-642 (Oct. 2002).
Blaha et al., "The slit lamp and the laser in ophthalmology—a new laser slit lamp", SPIE Optical Instrumentation for Biomedical Laser Applications, vol. 658, pp. 38-42, 1986.
Boppart, S., et al., "Intraoperative Assessment of Microsurgery with Three-dimensional Optical Coherence Tomography", Radiology, 208(1):81-86, Jul. 1998.
Davidson, "Analytic Waveguide Solutions and the Coherence Probe Microscope", Microelectronic Engineering, 13, pp. 523-526, 1991.
Drexler, W., et al., "Measurement of the thickness of fundus layers by partial coherence tomography", Optical Engineering, 34(3):701-710, Mar. 1995.
Dyer, R, et al., "Optical Fibre Delivery and Tissue Ablation Studies using a Pulsed Hydrogen Fluoride Laser", Lasers in Medical Science, 7:331-340, 1992.
Fercher et al., "In Vivo Optical Coherence Tomography", American Journal of Ophthalmology, 116(1), pp. 113-114, 1993.
Fujimoto, J., et al., :Biomedical Imaging using Optical Coherent Tomography, 1994, 67.
Hammer, D., "Ultrashort pulse laser induced bubble creation thresholds in ocular media", SPIE, 2391:30-40, 1995.
Hauger, C., et al., "High speed low coherence interferometer for optical coherence tomography", Proceedings of SPIE, 4619:1-9, 2002.
Hee, M., et al., "Optical Coherence tomography of the Human Retina", Arch Ophthalmol, 113:325-332; Mar. 1995.
Hitzenberger et al., "Interferometric Measurement of Corneal Thickness With Micrometer Precision", American Journal of Ophthalmology, 118:468-476, Oct. 1994.
Hitzenberger, C., et al., "Retinal layers located with a precision of 5 μm by partial coherence interferometry", SPIE, 2393:176-181, 1995.
Itoh et al., "Absolute measurements of 3-D shape using white-light interferometer", SPIE Interferometry: Techniques and Analysis, 1755:24-28, 1992.
Izatt et al., "Ophthalmic Diagnostics using Optical Coherence Tomography", SPIE Ophthalmic Technologies, 1877:136-144, 1993.
Izatt, J., et al., "Micrometer-Scale Resolution Imaging of the Anterior Eye In vivo With Optical Coherence Tomography", Arch Ophthalmol, 112:1584-1589, Dec. 1994.
Jean, B., et al., "Topography assisted photoablation", SPIE, vol. 3591:202-208, 1999.
Kamensky, V., et al., "In Situ Monitoring of Laser Modification Process in Human Cataractous Lens and Porcine Cornea Using Coherence Tomography", Journal of biomedical Optics, 4(1), 137-143, Jan. 1999.
Lee et al., "Profilometry with a coherence scanning microscope", Applied Optics, 29(26), 3784-3788, Sep. 10, 1990.
Lubatschowski, "The German Ministry of Research and education funded this OCT guided fs laser surgery in Sep. 2005", http://www.laser-zentrum-hannover.de/download/pdf/taetigkeitsbericht2005.pdf.
Massow, O., et al., "Femotosecond laser microsurgery system controlled by OCT", Laser Zentrum Hannover e.V., The German Ministry of education and research,19 slides, 2007.
Puliafito, Carmen, "Final technical Report: Air Force Grant #F49620-93-I-03337(1)" dated Feb. 12, 1997, 9 pages.
Ren, Q., et al., "Axicon: A New Laser Beam Delivery System for Corneal Surgery", IEEE Journal of Quantum Electronics, 26(12):2305-2308, Dec. 1990.
Ren, Q., et al., "Cataract Surgery with a Mid-Infrared Endo-laser System", SPIE Ophthalmic Technologies II, 1644:188-192, 1992.
Thompson, K., et al., "Therapeutic and Diagnostic Application of Lasers in Ophthalmology", Proceedings of the IEEE, 80(6):838-860, Jun. 1992.
Thrane, L, et al., "Calculation of the maximum obtainable probing depth of optical coherence tomography in tissue", Proceedings of SPIE, 3915:2-11, 2000.
Wisweh, H., et al., "OCT controlled vocal fold femtosecond laser microsurgery", Laser Zentrum Hannover e.V., The German Ministry of education and research, Grants: 13N8710 and 13N8712; 23 slides, 2008.

* cited by examiner

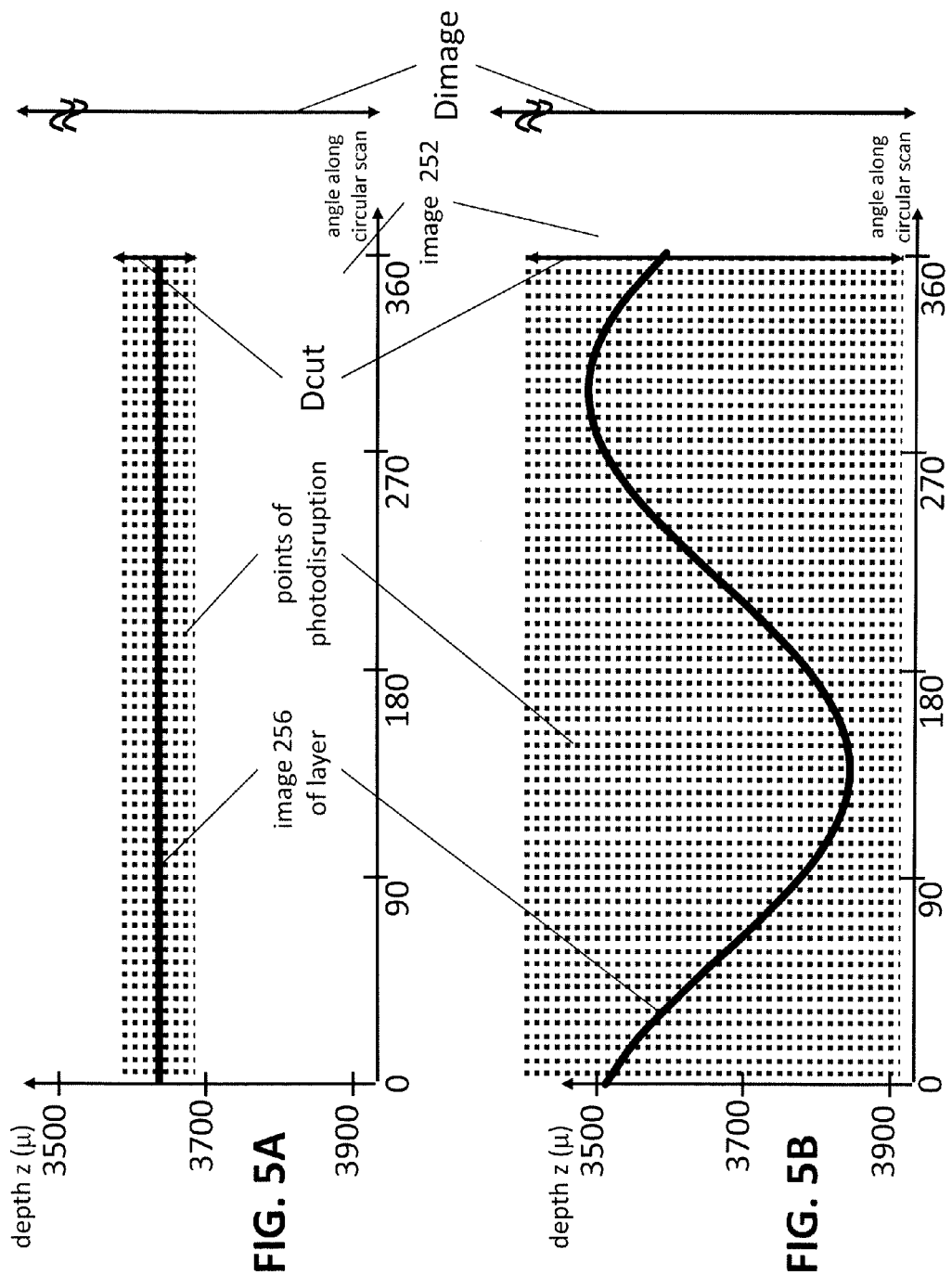

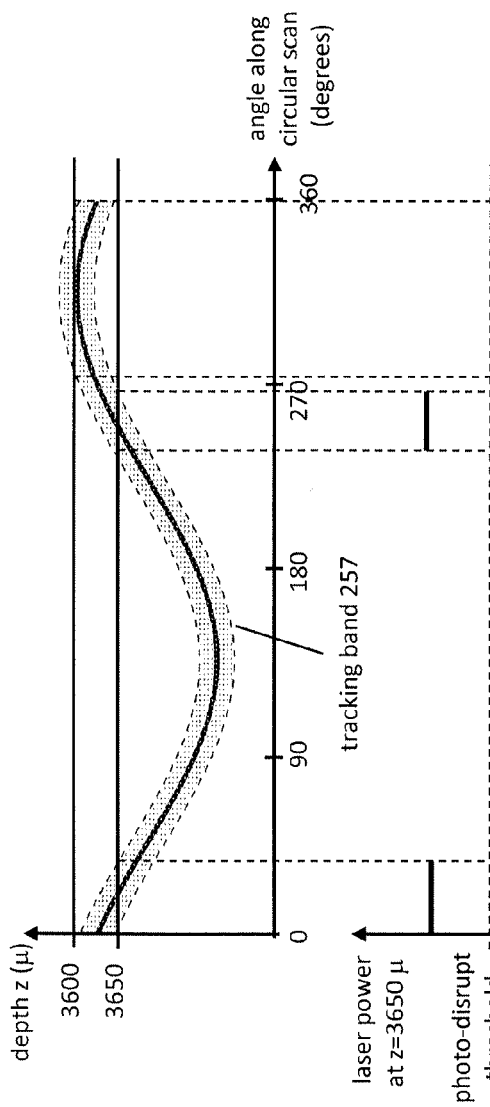
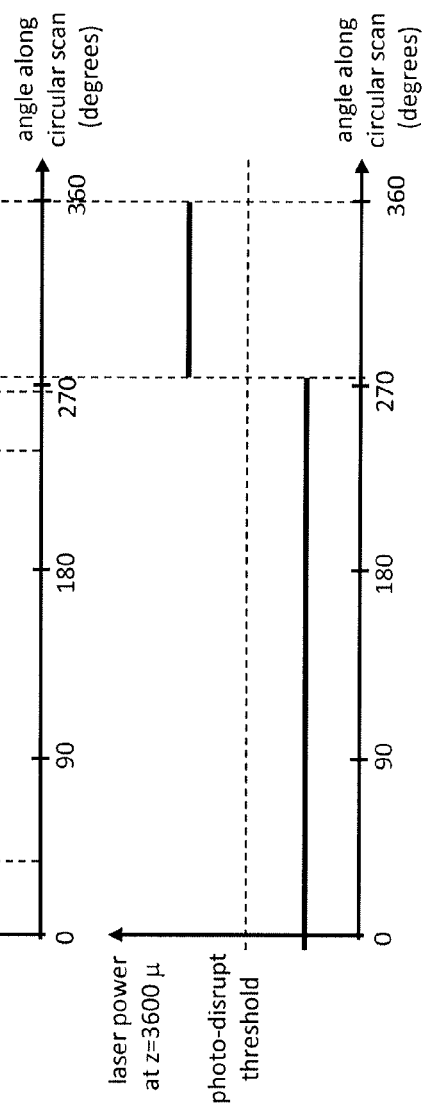
FIG. 6C
FIG. 6D
FIG. 6E

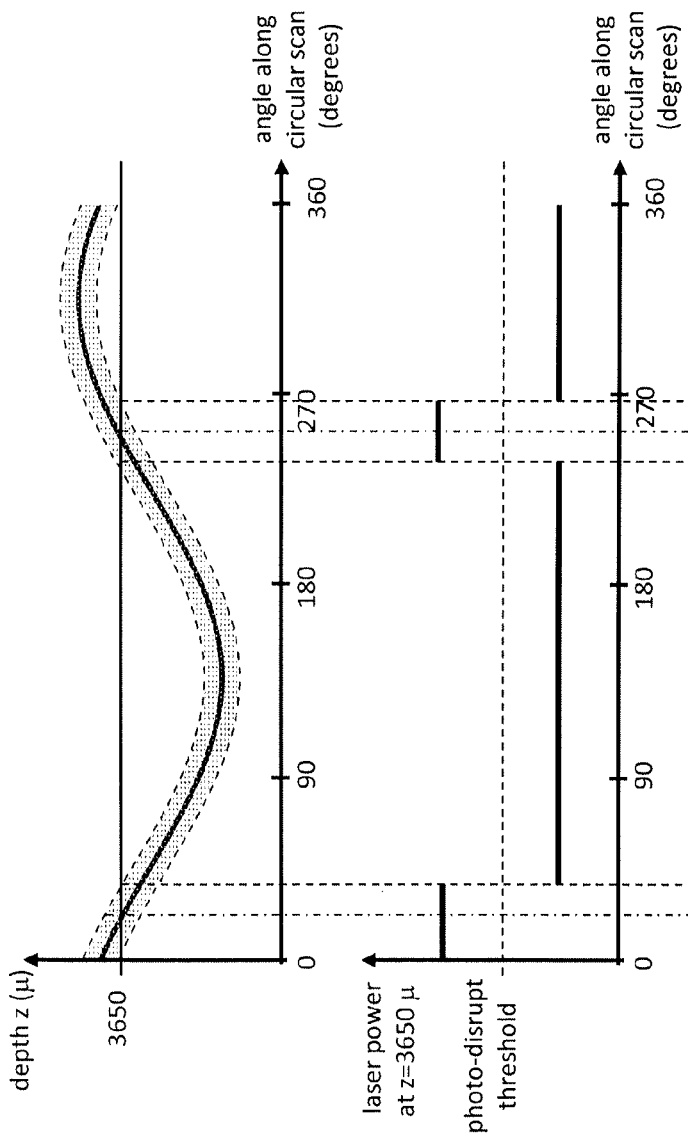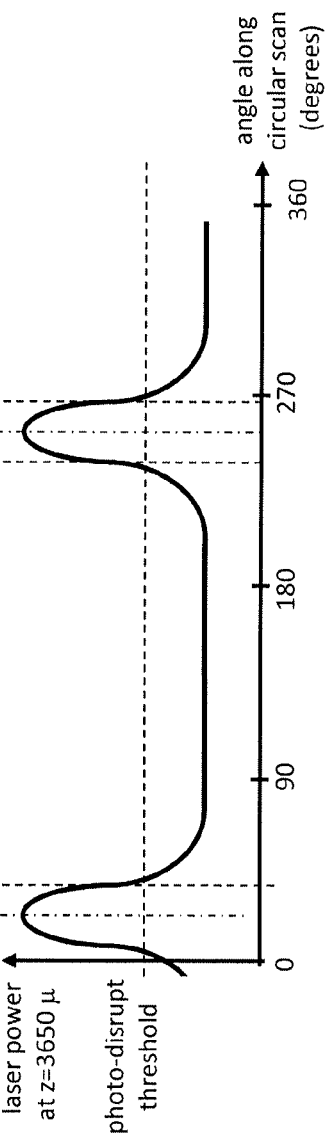
FIG. 6G
FIG. 6H

IMAGING-CONTROLLED LASER SURGICAL SYSTEM

TECHNICAL FIELD

This patent document describes a system and method for controlling a laser in an ophthalmic procedure. In more detail, this patent document describes an imaging-controlled laser system for controlling the power of a pulsed ophthalmic laser during capsulotomy and cataract procedures, among others.

BACKGROUND

Laser systems have become essential for ophthalmic surgery. They have been employed in corneal procedures for some time now with high precision and therefore considerable success. In very recent times applications for other ophthalmic procedures have been contemplated, including cataract procedures.

Lasers can be used for forming high precision cuts. These cuts are created by focusing or directing a rapid sequence of laser pulses to a scan-pattern or point-pattern. The points of the scan-pattern often form a line or layer and the laser pulses are directed to these points by a scanning system that includes deflection devices, mirrors and lenses whose alignment can be changed very quickly. In typical laser systems the pulses can have a duration or pulse length in the nanosecond, picosecond, or even femtosecond range. The pulse repetition rate can be in the kHz to hundreds of kHz range.

The power or energy of the laser pulses can be chosen to exceed a so-called photodisruption threshold. Laser pulses with a power above this threshold can disrupt the ophthalmic tissue at the target points, inducing the formation of bubbles. Lines or layers of these bubbles can weaken the mechanical connection between the tissue-portions on the opposite sides of the bubbles. Often the weakening is substantial, effectively cutting the tissue. Therefore, a subsequent manual procedure can completely separate the tissue portions with ease.

One ophthalmic procedure which could benefit from using such a high precision laser cutting system is cataract surgery. A typical cataract surgery involves a capsulotomy step and a lysis or lens fragmentation step. During lysis, energy is applied to a lens nucleus to liquefy it. During lens fragmentation, or phaco-fragmentation, the nucleus of the lens can be cut into several pieces by scanning the laser along cutting surfaces to enable the subsequent piece-by-piece removal of the nucleus. The capsulotomy involves forming a circular cut on the anterior portion of the capsular bag of the lens to allow the surgeon to access and remove the cut-up pieces of the nucleus.

To optimize surgical laser systems for these complex ophthalmic procedures is a great challenge. However, the optimization promises great returns in terms of the precision and efficacy of the surgical procedures.

SUMMARY

One of the challenges of laser cataract surgery is that the procedures of capsulotomy and lens fragmentation can interfere with each other. In advanced laser systems the precision of the surgery can be enhanced by imaging the ophthalmic target tissue prior to the surgery and guide the laser pulses based on the image. If the lens fragmentation is performed first, then, as a surgical by-product, the capsule is expanded considerably and unevenly by the substantial amount of bubbles formed inside the capsule. Therefore, after the lens fragmentation, the capsule and lens has to be imaged for a second time to guide the subsequent circular cut of the capsulotomy. However, imaging the severely photodisrupted and distorted lens can be challenging. Also, the repeated imaging procedure consumes precious surgical time, increasing the discomfort of the patient, potentially undermining the precision of the entire procedure.

On the other hand, if the capsulotomy is performed first, it creates a substantial amount of bubbles in the anterior region of the lens and in the anterior aqueous chamber of the eye. The amount of bubbles is especially high if the lens is in a tilted position before the procedure, as explained below. These bubbles can increase the scattering of the laser pulses of the subsequent lens fragmentation considerably as the subsequent pulses are directed to the inside of the lens and thus propagate through the bubble-rich anterior region. The increased scattering can again potentially undermine the precision of the cataract procedure.

Thus, both sequences of the lens fragmentation and capsulotomy have drawbacks, as the first step can reduce the precision and control of the subsequent step. Therefore, laser systems that reduce, resolve, or eliminate one or more of these drawbacks can offer advantages.

Embodiments of the present invention can provide advantageous functionalities in view of these challenges. In particular, an embodiment of an imaging-based laser system can include a laser-beam system, configured to generate and scan a beam of laser pulses with an adjustable laser-power parameter to points of a scan-pattern in an eye, and an imaging-based laser-controller, configured to image a layer in the eye, to control the scanning of the beam of laser pulses to the points of the scan-pattern, and to control a laser-power parameter of the laser pulses according to the distance of the points of the scan-pattern from the imaged layer.

An implementation of an imaging-based laser system can include a laser that generates and directs a beam of laser pulses into an eye, an imaging system that images a capsule layer of the eye, and a laser control system that controls the laser to direct the beam to spots within a tracking band of the imaged capsule layer with a laser-power parameter above a photo-disruption threshold, and to spots outside the tracking band of the imaged capsule layer with a laser-power parameter below a photo-disruption threshold, wherein the image-based laser system is configured to perform a capsulotomy before a lysis or lens- or phaco-fragmentation during a cataract procedure.

An implementation of an image-guided ophthalmic laser system can include a laser engine, configured to generate laser pulses, a beam modifier, configured to modify a laser-power parameter of the laser pulses, a laser scanner, configured to direct the laser pulses to scanning-points in an eye, an imaging system, configured to image a region in the eye, and a pattern generator, coupled to the imaging system, the beam modifier and the laser scanner, configured to generate coordinates of the scanning-points for the laser scanner, and to associate a laser-power parameter with the scanning-points depending on a distance of the scanning-points from a target-pattern.

In some implementations, a method of performing an imaging-controlled ophthalmic procedure can include imaging a layer in an eye, generating coordinates of points of a scan-pattern, determining a distance of the points of the scan-pattern from the imaged layer, and associating laser-power parameters with the points based on the determined distance.

BRIEF DESCRIPTION OF THE DRAWINGS

FIGS. 5A-B illustrate traditional scan-patterns for non-tilted and tilted lenses as a function of a scanning variable.

FIGS. 6A-H illustrate a scan-pattern along a circular scan with a distance-dependent laser-power parameter.

DETAILED DESCRIPTION

Implementations and embodiments described in this patent document offer improvements for the above described challenges.

Figure 1:
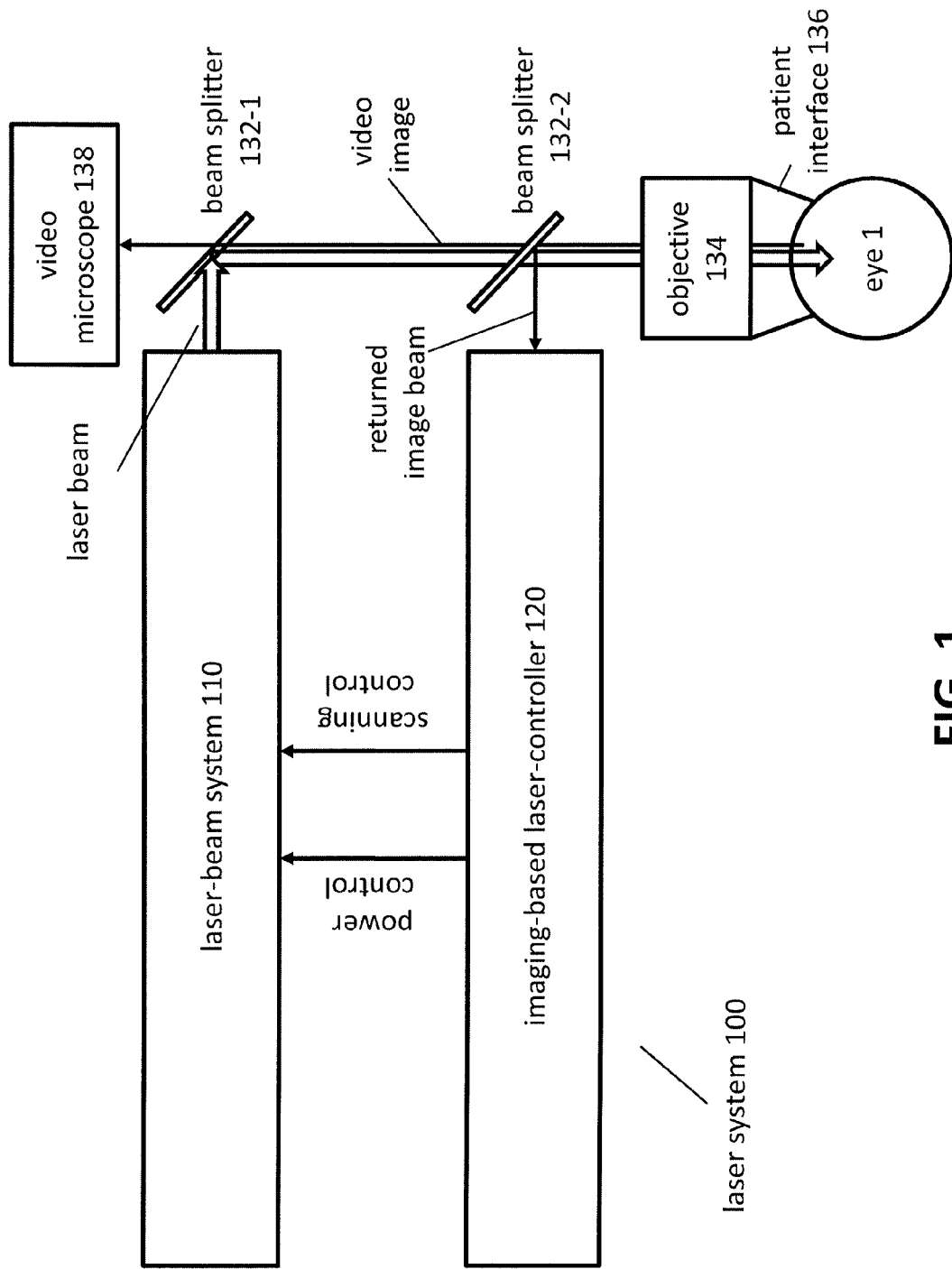
FIG. 1 illustrates an embodiment of a surgical laser system with an imaging-controlled laser system

FIG. 1 illustrates an imaging-based laser system 100, including a laser-beam system 110 to generate and scan a beam of laser pulses with an adjustable laser-power parameter to points of a scan-pattern in an eye 1, and an imaging-based laser-controller 120 to image a layer in the eye, to control the scanning of the beam of laser pulses to the points of the scan-pattern, and to control a laser-power parameter of the laser pulses according to the distance of the points of the scan-pattern from the imaged layer. The laser-controller 120 can perform these functions by sending a power control signal and a scanning control signal to the laser-beam system 110, for example.

The laser beam of the laser-beam system 110 can be guided into the main optical pathway at a beam-splitter 132-1 that can redirect the beam to an objective 134. The beam can propagate through the objective 134 and through a patient interface 136 to enter into the surgical eye 1.

The surgery can be assisted by imaging the eye 1 with various techniques. A visible imaging light can be used to create a video image that is processed by a video microscope 138. In addition, the imaging-based laser-controller 120 can shine an imaging beam on the eye and form an image based on the returned image beam. This imaging beam can be coupled into and out of the main optical path by a beam-splitter 132-2.

FIGS. 2A-D illustrate various embodiments of the laser-beam system 110.

Figure 2A:
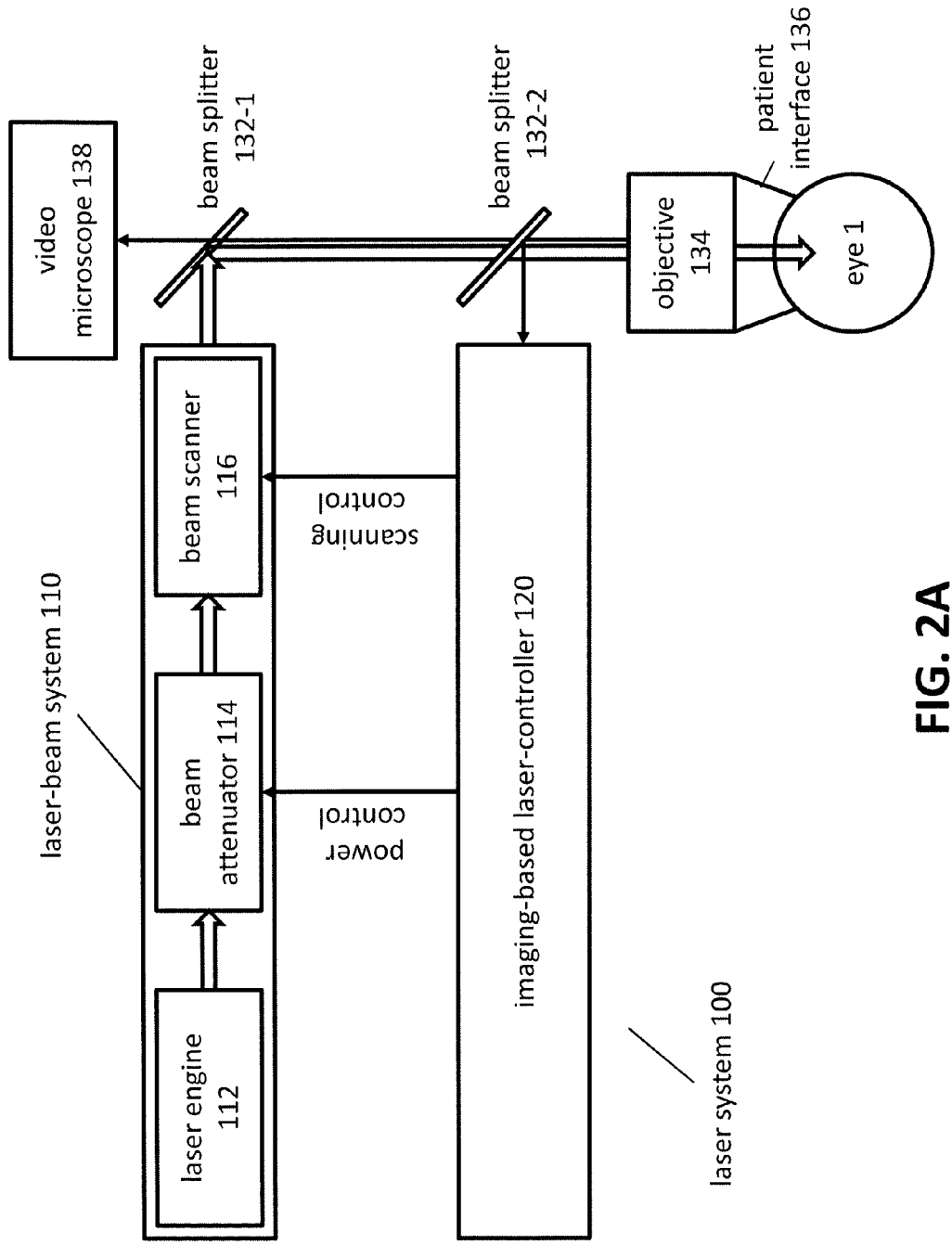
FIGS. 2A-D illustrate embodiments of the laser-beam system.

FIG. 2A illustrates that embodiments of the laser-beam system 110 can include a laser engine 112 to generate the beam of laser pulses, a beam attenuator 114 to modify the laser-power parameter of the laser pulses, and a beam scanner 116 to direct the beam of laser pulses to the points of the scan-pattern in the eye. The laser engine 112 can generate laser pulses with a duration of nanoseconds, picoseconds or even femtoseconds, i.e. in the $10^{-9}$-$10^{-15}$ sec range. These pulses can be generated at a repetition rate in a wide range of frequencies: from 0.1 kHz to 1,000 kHz, or in a range of 1 kHz to 500 kHz, or in some implementations in the 10 kHz to 100 kHz range. The power control signal of the laser-controller 120 can be coupled into the beam attenuator 114 and the scanning control signal of the laser-controller 120 can be coupled into the beam scanner 116.

The beam attenuator 114 can include a Pockels cell, a polarizer-assembly, a mechanical shutter, an electro-mechanical shutter, or an energy wheel. Each of these implementations can modify a laser-power parameter of the laser pulses. The laser-power parameter can be a pulse energy, a pulse power, a pulse length or a pulse repetition rate of the laser pulses, among others. The beam attenuator 114 can modify one or more of these laser-power parameters. In a simple implementation, the beam attenuator 114 can shutter or block selected laser pulses. In another, a polarizer assembly can reduce the power of selected laser pulses by adjusting the relative angle of subsequent polarizing filters.

In the embodiment of FIG. 2A, the beam attenuator 114 can be located between the laser engine 112 and the beam scanner 116 in the path of the laser beam.

Figure 2B:
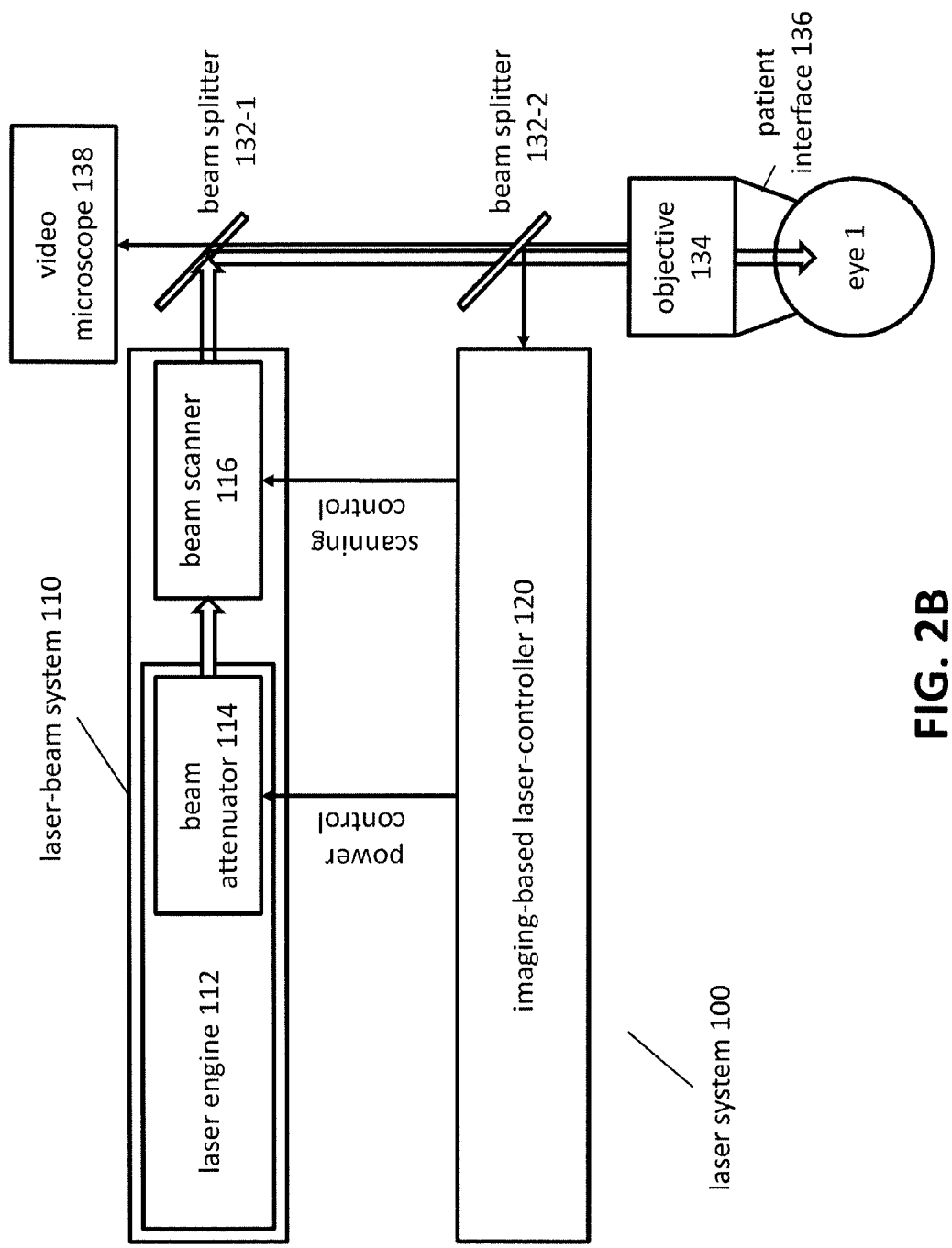

FIG. 2B illustrates and embodiment in which the beam attenuator 114 is at least partially integrated into the laser engine 112. In some cases, the beam attenuator 114 can be part of the laser engine 112. For example, a Pockels cell within the laser engine 112 can be the beam attenuator 114.

Figure 2C:
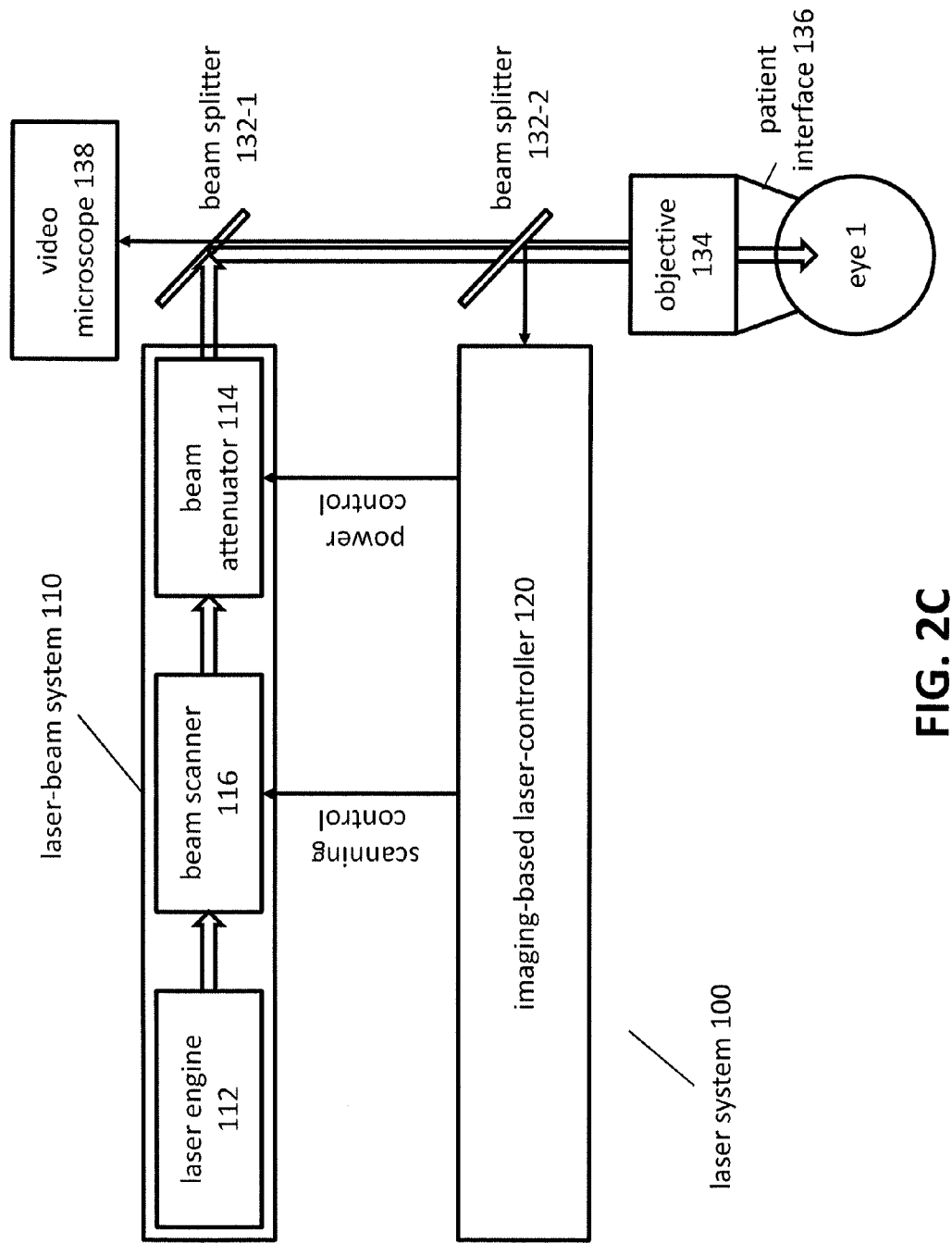

FIG. 2C illustrates and embodiment in which the beam attenuator 114 is located after the beam scanner 116 in the path of the laser beam.

Figure 2D:
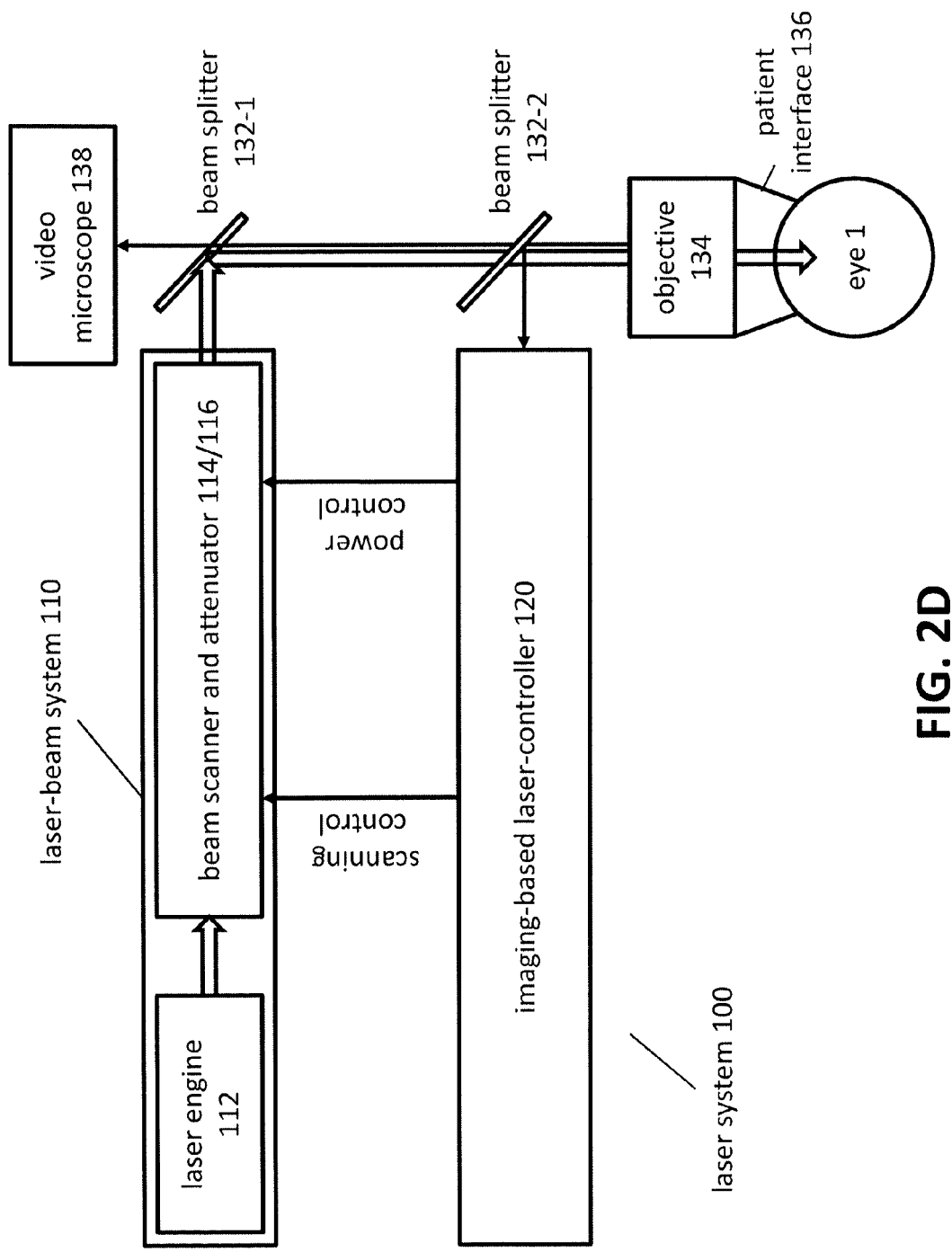

Finally, FIG. 2D illustrates an embodiment in which the beam attenuator 114 and the beam scanner 116 are at least partially integrated.

FIGS. 3A-E illustrate various embodiments of the imaging-based laser-controller 120.

Figure 3A:
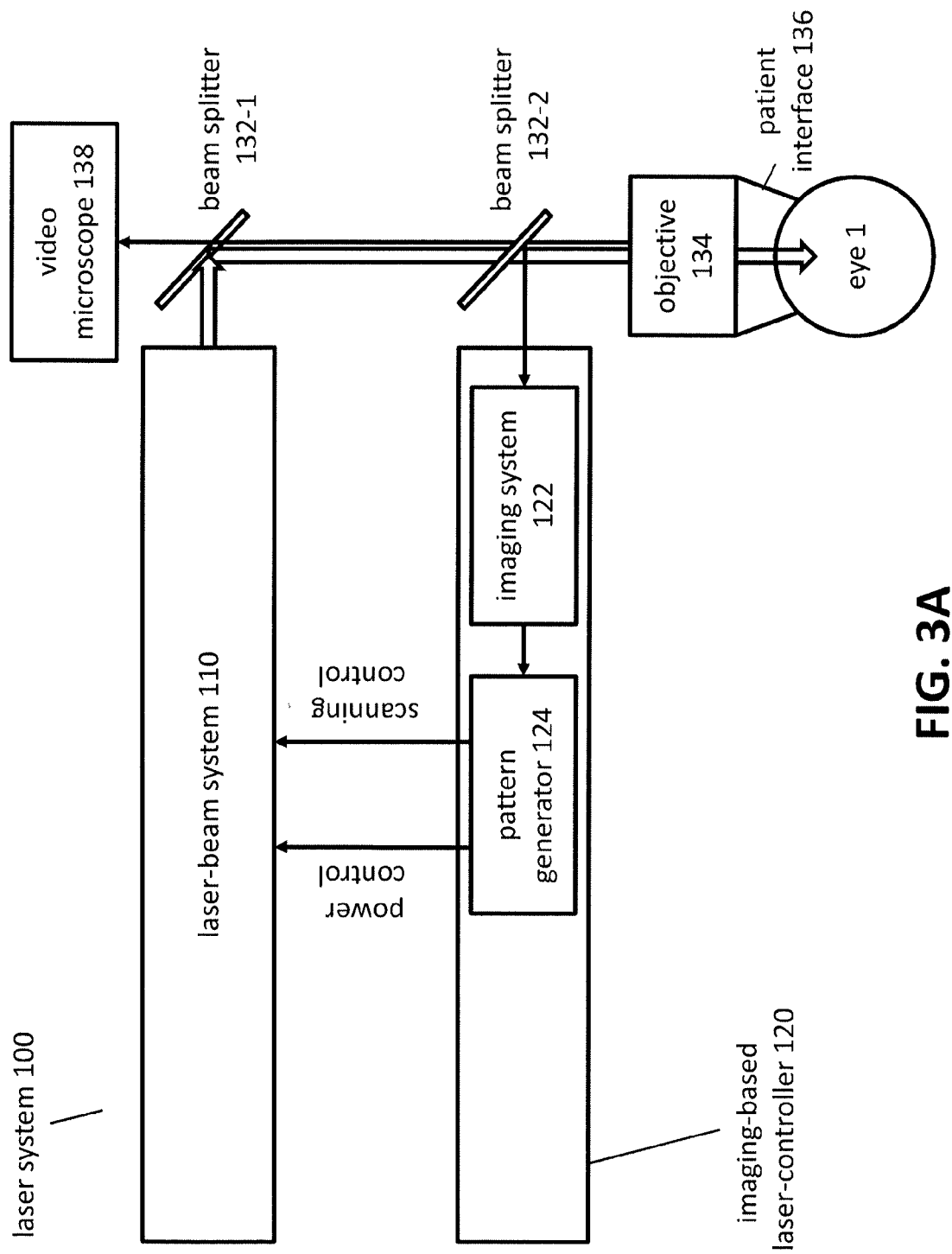
FIGS. 3A-E illustrate embodiments of the imaging-based laser controller.

FIG. 3A illustrates that the laser-controller 120 can include an imaging system 122 to image the imaged layer in the eye and a pattern generator 124 to generate coordinates of the points of the scan-pattern, to associate laser-power parameters with the points depending on the distance of the points from the imaged layer, and to signal the generated coordinates of the points and the corresponding laser-power parameters to the laser-beam system 110. In some implementations, the imaging system 122 can image any ophthalmic target in the anterior or posterior segment of the eye, targets from the cornea to the retina.

The pattern generator 124 can signal the generated coordinates of the points of the scan-pattern to the beam scanner 116 with a scanning control signal. Further, the pattern generator 124 can signal the laser-power parameters corresponding to the points of the scan-pattern to the beam attenuator 114 with a power control signal. The laser-power parameter can be a pulse energy, a pulse power, a pulse length or a pulse repetition rate of the laser pulses.

The imaging system 122 can include an ophthalmic coherence tomography (OCT) system, a Scheimpflug imaging system, a scanning imaging system, a single shot imaging system, an ultrasound imaging system, and a video imaging system. Here, the scanning imaging systems can create the image by scanning an imaging beam, whereas single shot imaging systems can acquire imaging information about an imaged area or volume in a single shot. The OCT system can be a time-domain OCT, a frequency-domain OCT, or a spectrometer-based OCT system, among others.

Figure 3B:
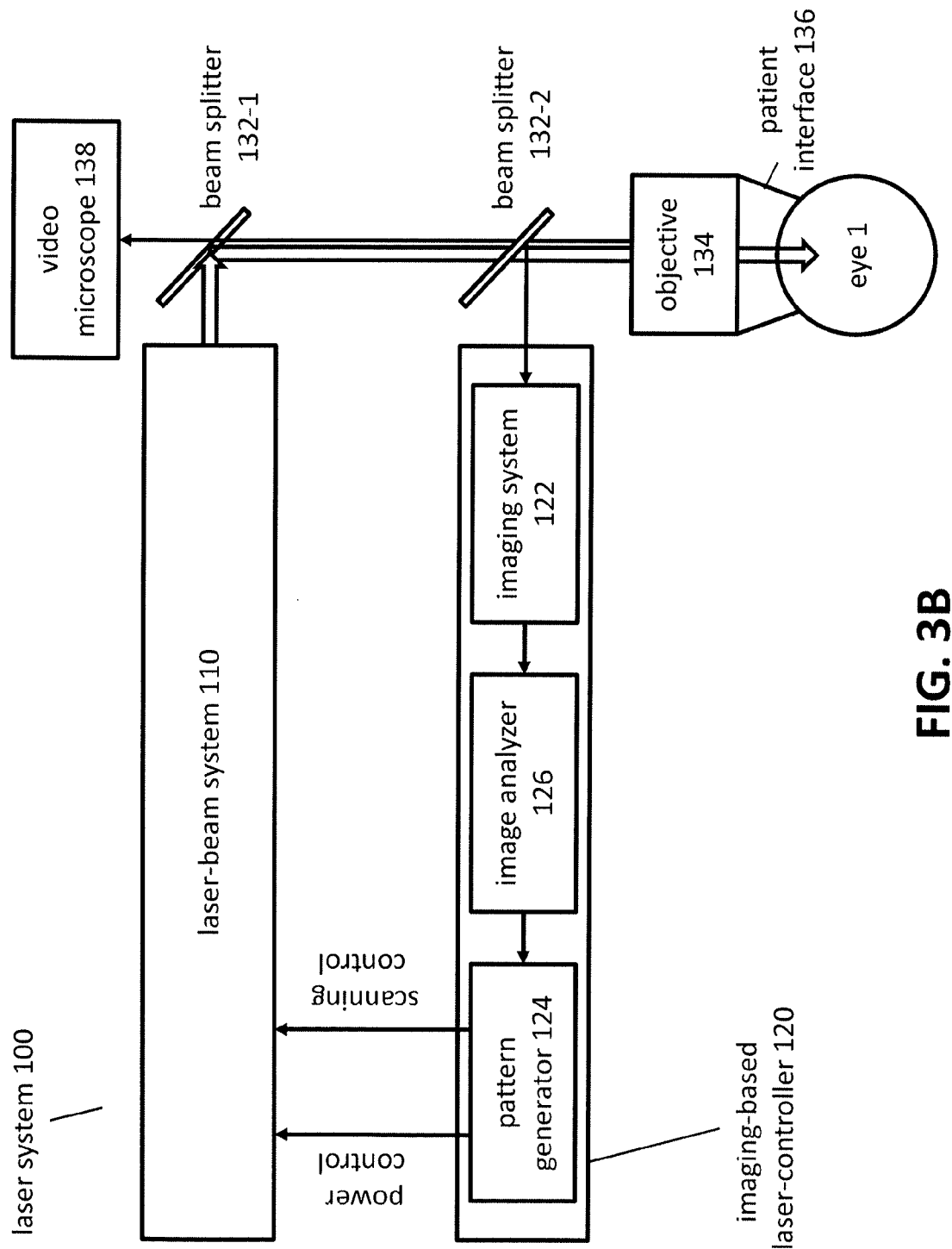

FIG. 3B illustrates that in some implementations the laser-controller 120 can include an image-analyzer 126. The image analyzer 126 can receive the image of the imaged layer from the imaging system 122, perform an analysis of the imaged layer as described below and forward the result of the analysis to the pattern generator 124.

Figure 3C:
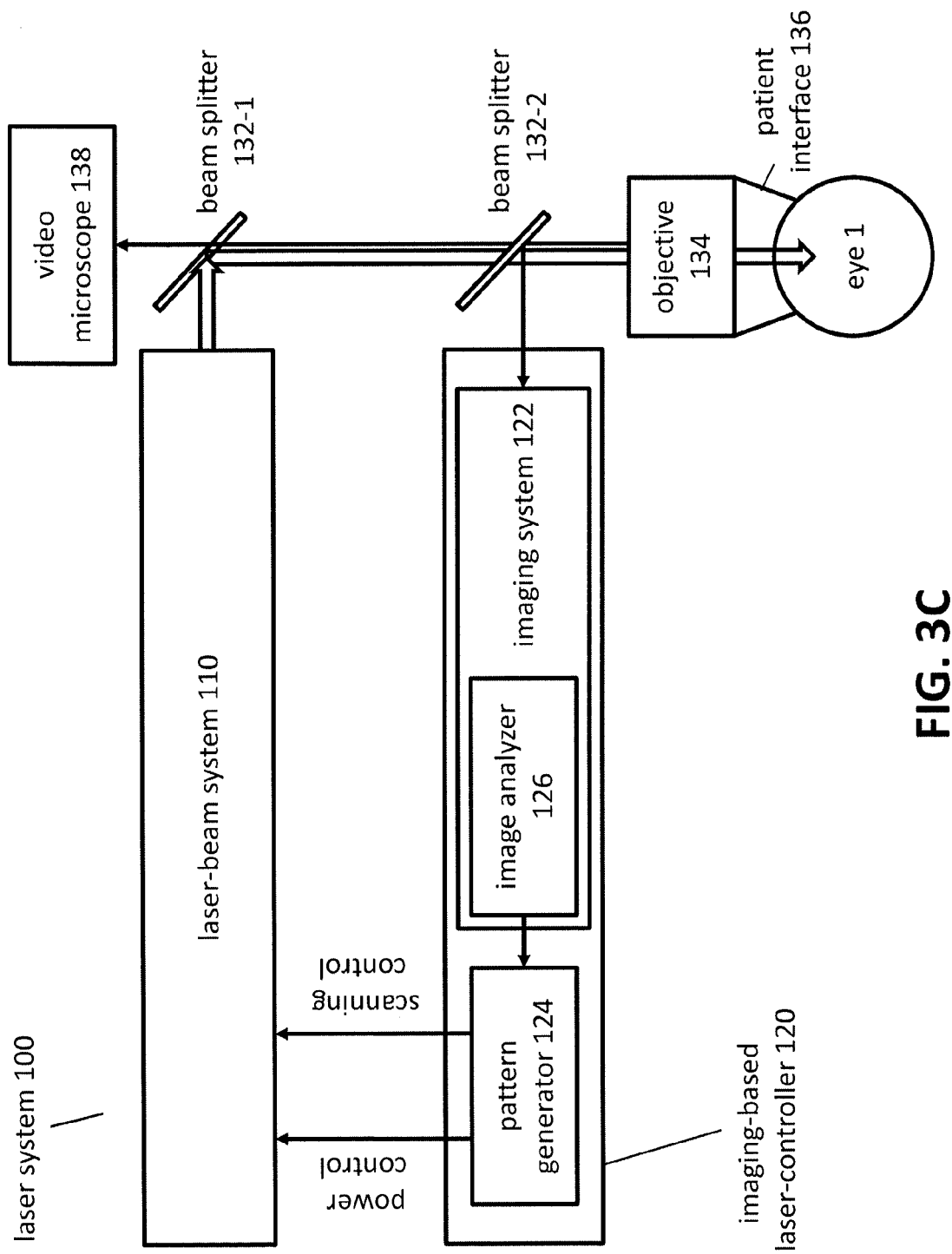
Figure 3D:
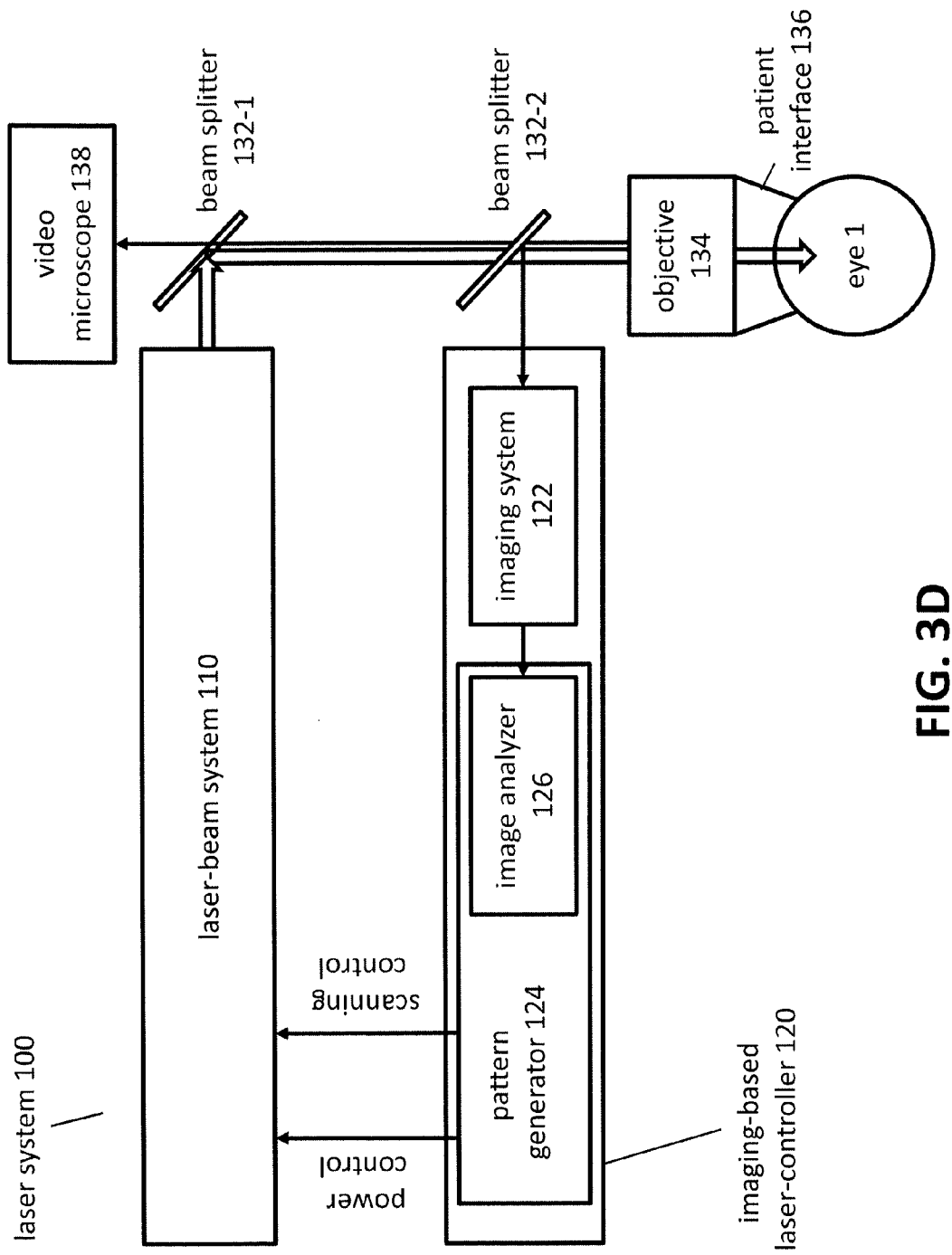

FIG. 3C illustrates that in some implementations the image analyzer 126 can be at least partially integrated with the imaging system 122. FIG. 3D illustrates that in some implementations the image analyzer 126 can be at least partially integrated with the pattern generator 124.

Figure 3E:
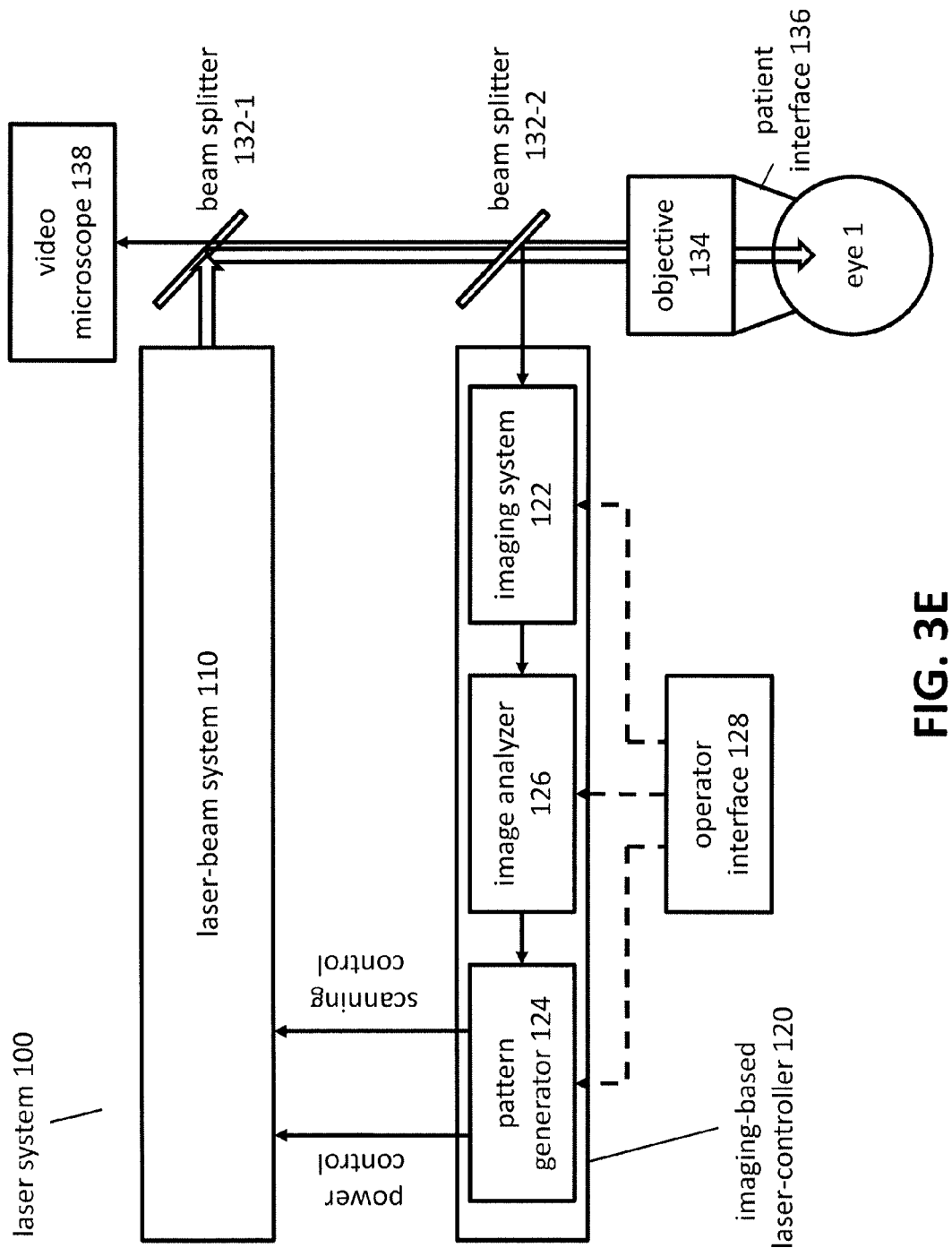

FIG. 3E illustrates that in some embodiments, the laser system 100 can include an operator-interface 128 that can be coupled to one or more of the imaging system 122, the pattern generator 124 and the image analyzer 126.

Figure 4A:
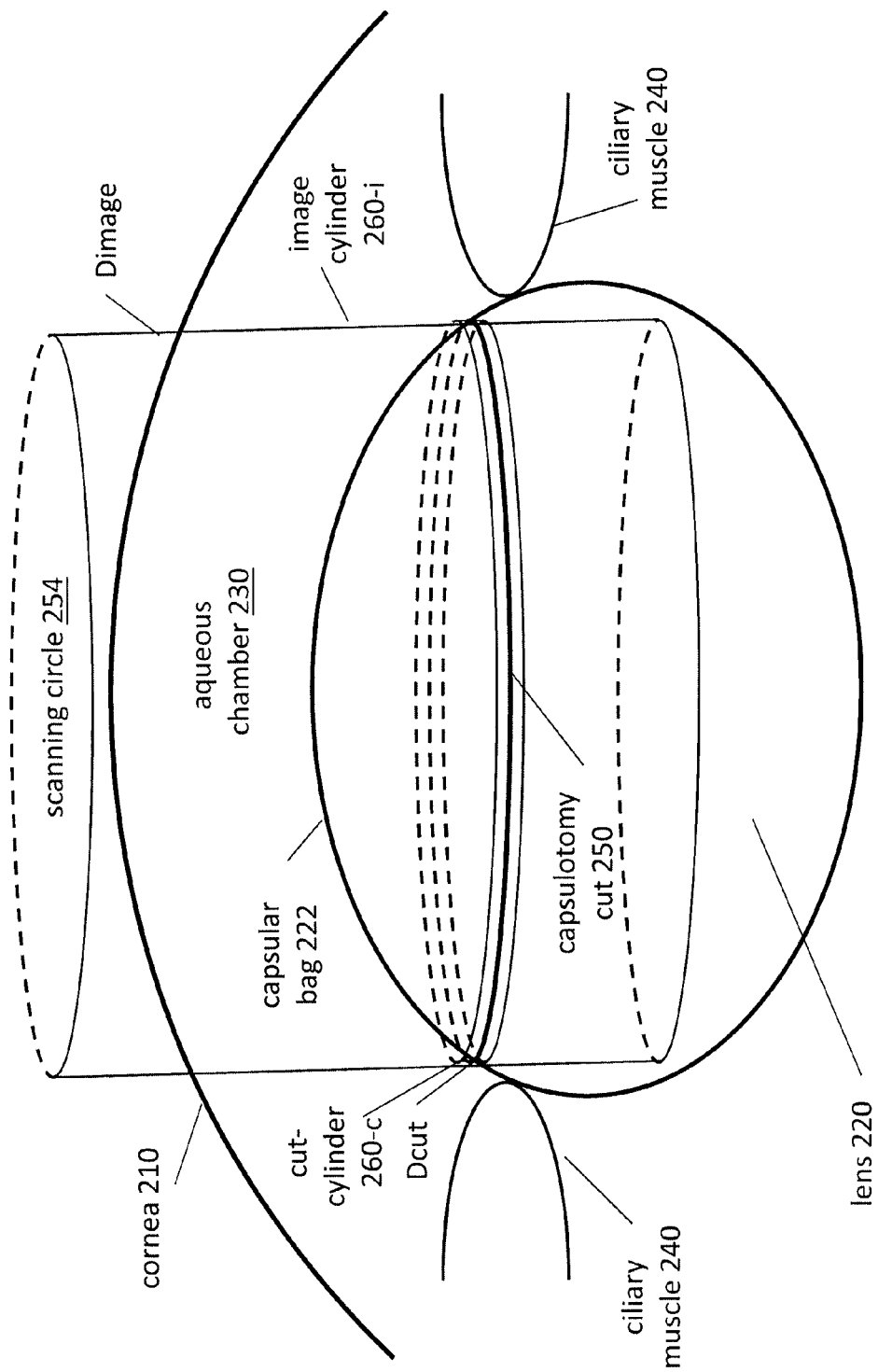
FIGS. 4A-B illustrate the scan-patterns for non-tilted and tilted lenses.
Figure 4B:
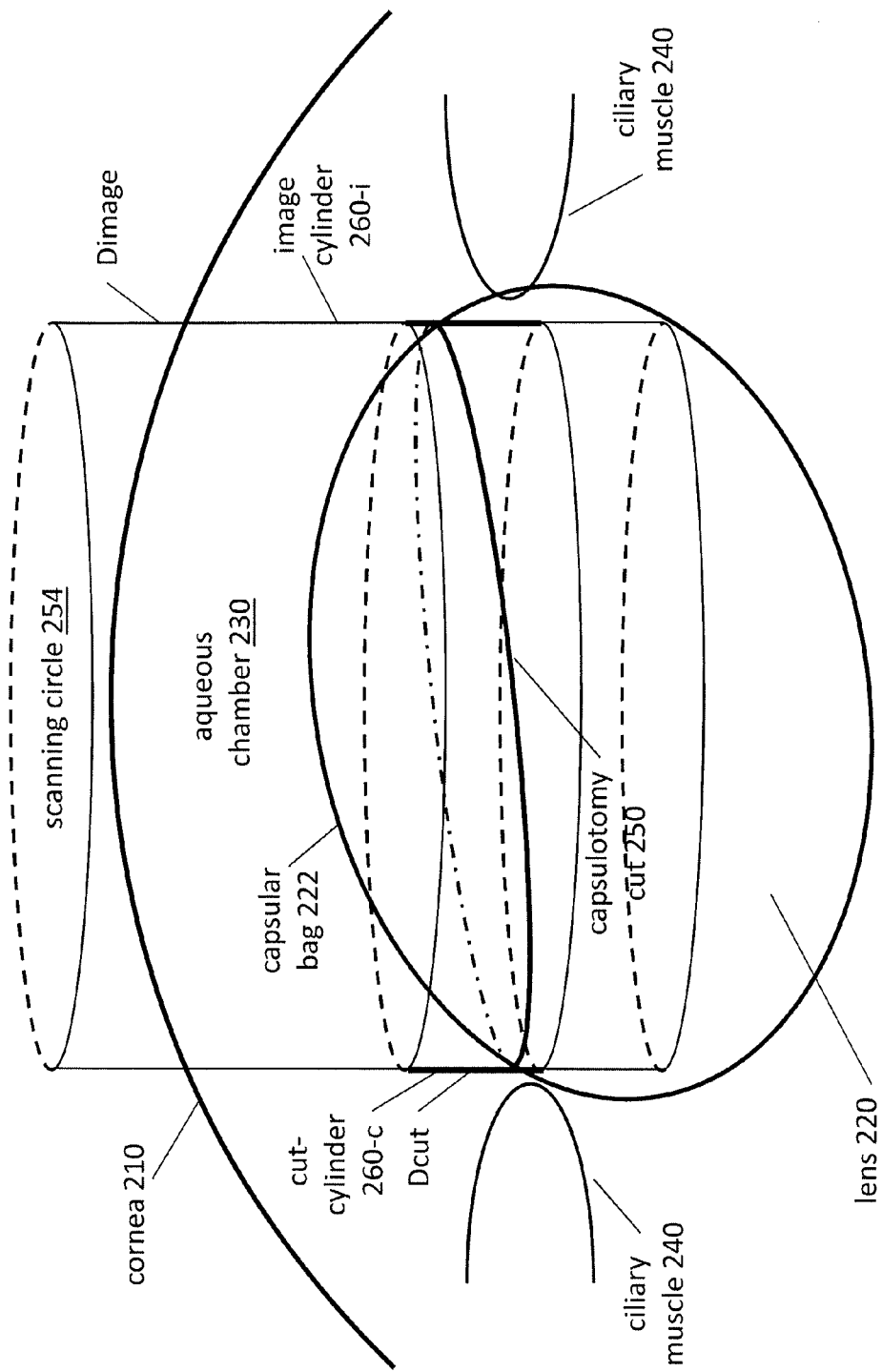

FIGS. 4A-B set the stage to illustrate the operation of the laser system 100. The imaging system 122 can image the imaged layer in an image region that can be based on a loop, an arc, a line, or a two-dimensional pattern transverse to a z-axis of the imaging system, and extends to a depth range Dimage along the z-axis of the imaging system. The imaging system 122 can support a determination of a z-depth coordinate of the imaged layer corresponding to a scanning coordinate along an image-scan.

FIG. 4A illustrates that the imaging system 122 can perform an imaging relevant for a capsulotomy step of a cataract procedure. The schematic cross section illustrates the anterior segment of the eye 1. The outermost layer is a cornea 210. A crystalline lens 220 is located behind the cornea 210, separated from it by an aqueous anterior chamber 230. The crystalline lens 220 is encapsulated in a thin capsule or capsular bag 222. The lens 220 is held in place by ciliary muscles 240. These muscles 240 also adjust the shape of the crystalline lens 220 as needed for bringing objects into focus.

As it has been described above, in order to facilitate the removal of a fragmented nucleus of the lens 220, the cataract surgery typically involves creating a circular capsulotomy cut 250 on the capsular bag 222. As a first step, the imaging system 122 can create an image 252 of the anterior segment of the eye by scanning along a scanning circle 254 and imaging the eye in a depth-range Dimage, defining an image-cylinder 260-i.

FIG. 5A illustrates that the image 252 typically includes an image 256 of the imaged anterior capsule layer of the lens 220 "unfolded" along a scanning variable, such as an angle along the circumference of the scanning circle 254. If a z-axis of the lens 220 is aligned with a z-axis of the laser system 100, the image 256 of the imaged layer is a flat line, indicating an essentially constant z-depth.

In other implementations, the image 252 can include the image of other ophthalmic targets, including corneal layers, portions of the sclera and even retinal layers. The zero depth level can be defined in a large number of ways, using a lens of the objective 134, a reference mirror of the imaging system 122, a level of the patient interface 136, or a level of an ophthalmic structure, such as the cornea 210.

By analyzing the image 252, a surgeon can recognize the image 256 of the imaged layer. Based on the z-depth of the imaged layer, the surgeon can decide where to direct the cutting laser beam to form the capsulotomy cut 250. The cutting laser beam is typically scanned along the same scanning circle 254 to form a cut-cylinder 260-c with a depth-range Dcut, typically smaller than Dimage. This way the placement of the cut-cylinder 260-c benefits maximally from the information contained in the image 252, and in particular in the image 256 of the imaged layer. The capsulotomy cut 250 is formed where the cut-cylinder 260-c intersects the lens capsule 222. In practice, the cut cylinder 260-c is often formed as a stack of bubble-circles, where the individual circles are created by directing the laser pulses along a circular scan-pattern at a fixed z-depth to cause photodisruption, followed by the formation of a similar circle at a slightly lesser z-depth.

In some typical cases, the image depth-range Dimage can be 5-10 millimeters, whereas the cut depth-range Dcut can be in the range of 50-200 microns, in some cases 75-150 microns, sometimes approximately 100 microns.

It is noted that the bubbles of the cut-cylinder 260-c can scatter and deflect laser pulses applied in subsequent surgical steps. For example, in a cataract surgery the capsulotomy can be followed by the lens fragmentation or lysis. The bubbles of the cut-cylinder 260-c can negatively impact the precision and efficiency of this subsequent lens-fragmentation by scattering the lens-fragmenting laser pulses.

Fortunately, when a z-axis of the lens 220 is parallel to a z-axis of the laser system 100, the depth range Dcut of the cut cylinder 260-c can be as little as 100 microns, creating only a limited number of bubbles. Thus, in the case of a well-aligned lens 220, the bubbles of the cut-cylinder 260-c introduce only a limited amount of scatter for the subsequent lens fragmentation laser pulses.

FIG. 4B illustrates, however, that in the typical surgical case the crystalline lens 220 can be tilted. This situation can occur for a variety of reasons. For example, the weight of the objective 134 can push the lens 220 sideways upon docking to the eye 1. Or, applying suction at the patient interface 136 to immobilize the eye 1 can lead to a tilting of the lens 220 as well.

FIG. 5B illustrates the image 252 of such a tilted lens 220 unfolded along the angular scanning variable of the scanning circle 254. In contrast to the non-tilted case of FIG. 5A, the image 256 of the tilted imaged layer can exhibit substantial sinusoidal oscillations. The amplitude of these oscillations can be as much as 300-500 microns. To make sure that the capsular bag 222 is cut everywhere along this sinusoid, the cut-cylinder 260-c can be formed with a much enlarged depth-range Dcut, exceeding the amplitude of the sinusoid. In the above example, Dcut can be 400-600 microns to be sure that the capsular bag 222 was cut along the entire sinusoid. Clearly, this approach may create 4-6 times more photodisrupted bubbles during capsulotomy than the procedure for a non-tilted lens. Capsulotomy bubbles in such an increased number can scatter the laser pulses of the subsequent lens fragmentation to a substantial degree, threatening its precision and efficacy.

FIGS. 6A-H illustrate that some implementations of the laser system 100 can substantially reduce the number of photodisrupted bubbles by generating bubbles only in a narrow proximity of the imaged layer.

As described above, this outcome can be achieved, for example, by the imaging-based laser-controller 120 imaging the capsular bag 222, controlling the scanning of the beam of laser pulses to the points of the scan-pattern, and controlling a laser-power parameter of the laser pulses according to the distance of the points of the scan-pattern from the imaged layer.

Figure 6A:
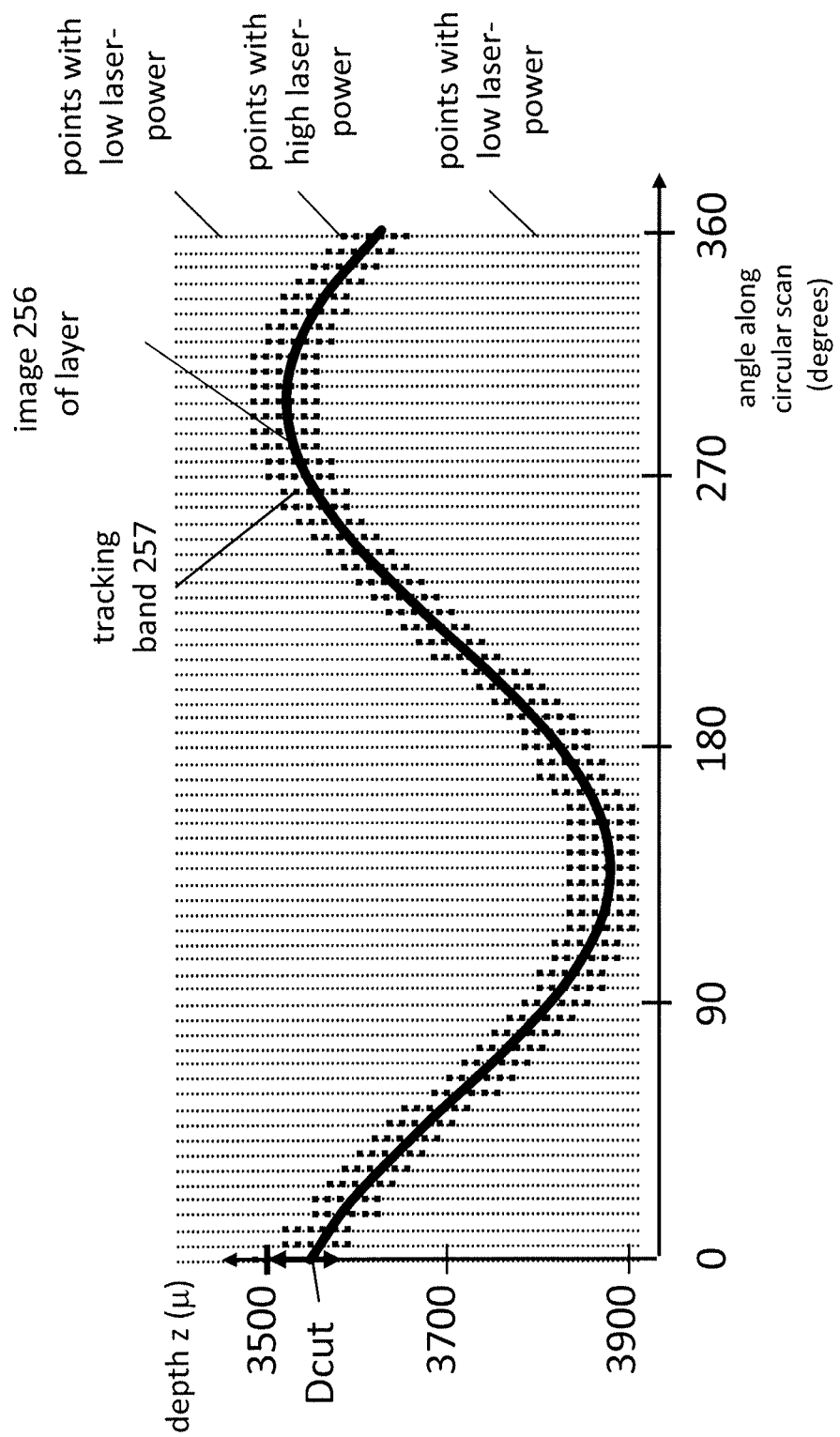
Figure 6B:
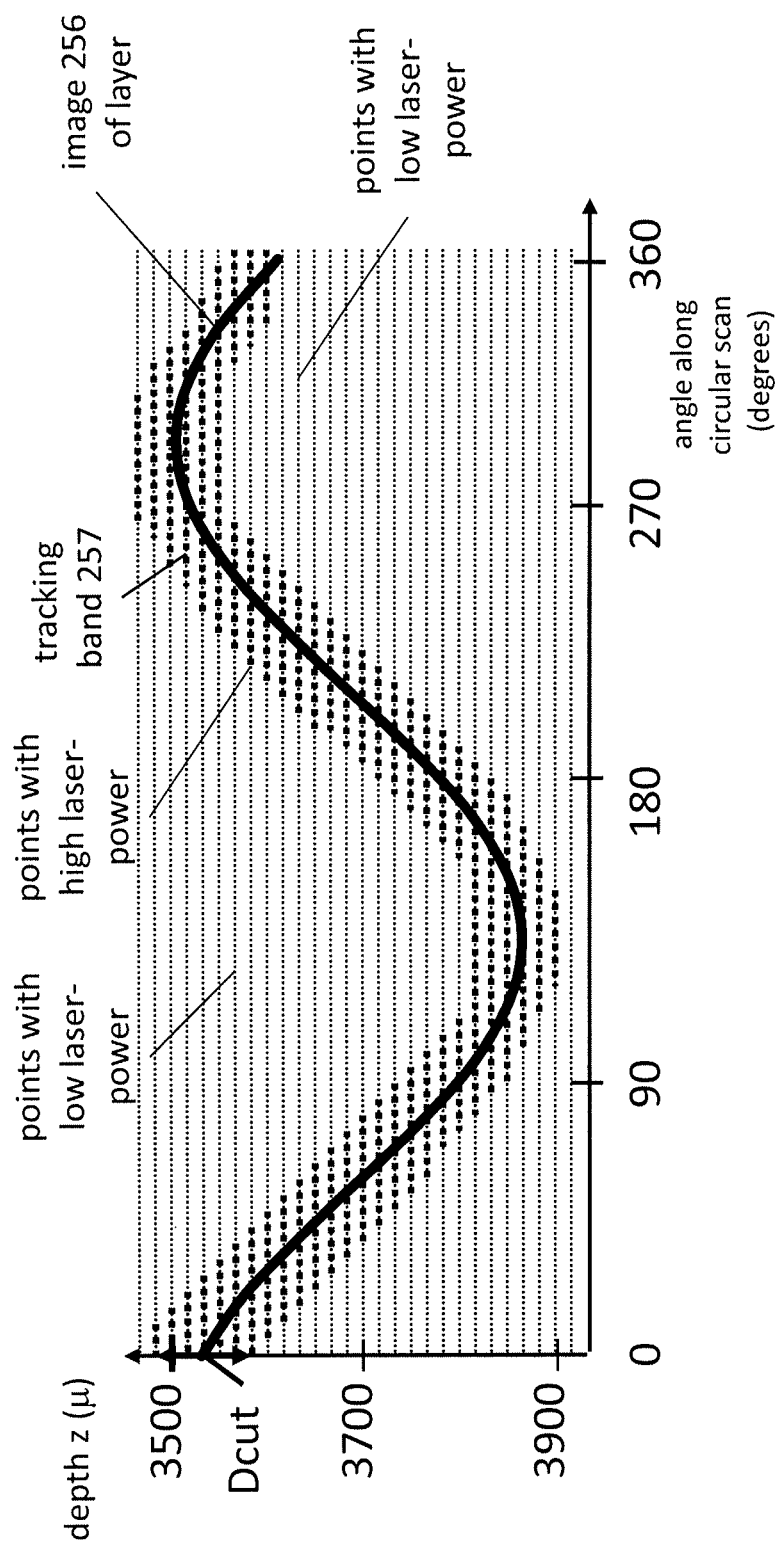

FIGS. 6A-B illustrate that as the laser pulses are directed to points of the scan-pattern, the laser controller 120 can modify or adjust a laser-power parameter of the pulses. In particular, when a laser pulse is directed to a point of the scan pattern that is within a Dcut distance from the image 256 of the imaged layer along the z axis, the laser-controller 120 can adjust its laser-power parameter to a high value, e.g. above a photodisruption threshold. Whereas, when a laser pulse is directed to a point of the scan pattern that is farther than Dcut from the image 256 of the imaged layer, the laser-controller 120 can adjust its laser-power parameter value to a low value, such as below a photodisruption threshold.

The just-described method creates bubbles only in a Dcut proximity of the imaged layer and therefore substantially reduces the number of bubbles to a value close to the number of bubbles for a well-aligned lens. For this reason, the scattering of the subsequent lens-fragmenting laser pulses by these capsulotomy bubbles is substantially reduced. Using the earlier value of Dcut being 400-600 microns for a tilted lens and 100 microns for a non-tilted lens, the present method may reduce the scattering of the lens-fragmenting bubbles by a factor of 4-6: a considerable gain in precision and control.

FIG. 6A illustrates the implementation when the scanning of the capsulotomy laser pulses of the scan-pattern is performed along the z-axis for fixed points of the circular scan. FIG. 6B illustrates the implementation when the scanning is performed along the circular scan with a fixed z-depth. This implementation can be used to create the above mentioned stacked circles. In either implementation, the points with high laser-power are placed within a tracking band 257 with a z-extent of Dcut.

FIGS. 6C-E illustrate the implementation when the laser pulses are scanned at fixed z-depths along the circular scan. A tracking band 257 can be defined as the set of points of the scan-pattern that are within the preselected distance Dcut from the image 256 of the imaged layer.

FIGS. 6D-E illustrate the laser power parameter of the pulses along the circular scan at two selected z-depths of 3600 microns and 3650 microns in an unfolded representation. The laser-controller 120 can control the laser power of the pulses that are directed to points inside the tracking band 257 to be above a photo-disruption threshold, and the laser power of the pulses that are directed to points outside the tracking band 257 to be below the photo-disruption threshold. In this embodiment, photodisrupted bubbles are only generated at points within the tracking band 257, achieving the above functionality of the laser system 100.

Figure 6F:
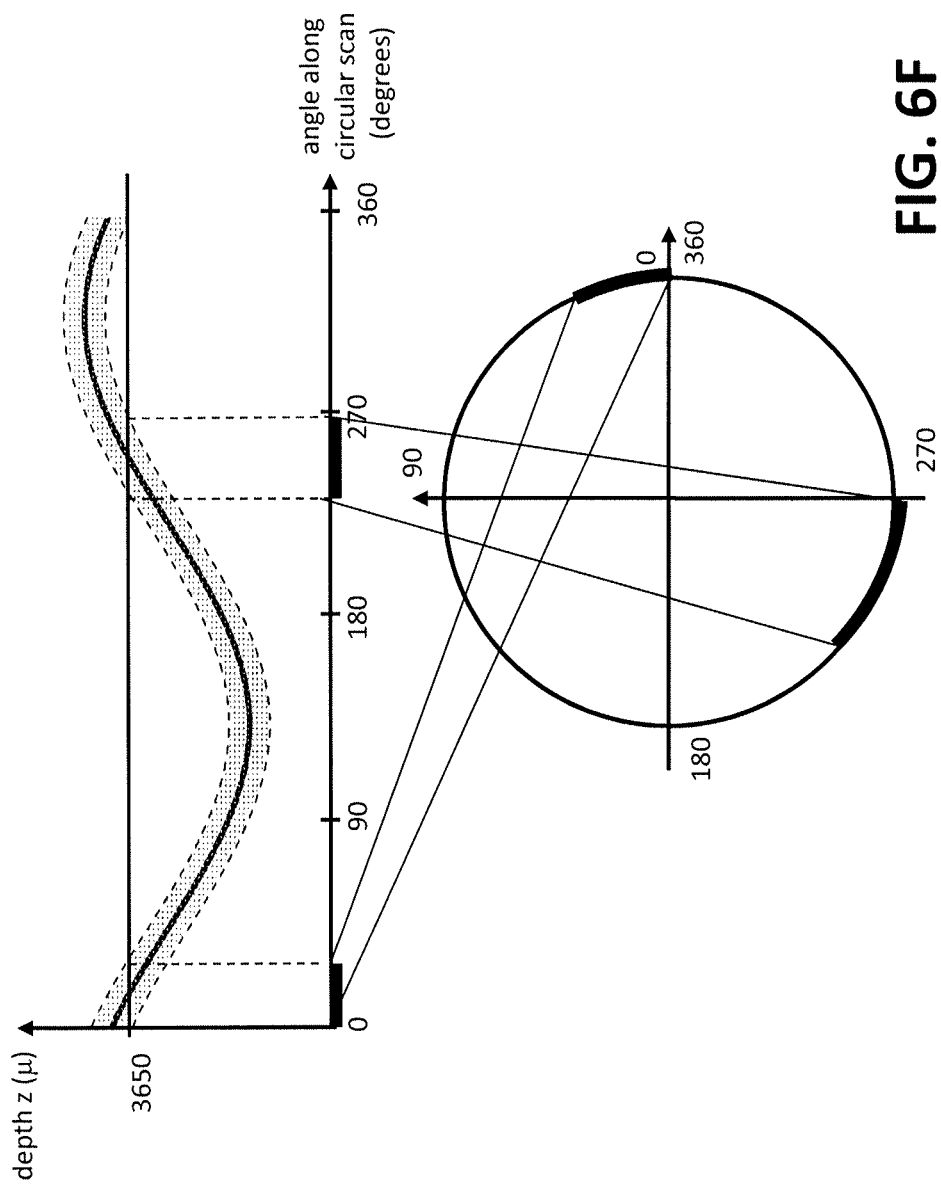

FIG. 6F expresses the same operation in a folded representation. Here the value of the laser power parameter is shown as a function of the angular scanning variable (typically the angle), projected on the scanning circle 254 itself. Again, for those points of the scan-pattern that lie within the tracking band 257, the laser power is high—indicated by a thick line—whereas for those points that lie outside the tracking band 257, the laser power is low.

FIGS. 6G-H illustrate a related implementation, where the laser-power controller 120 controls the laser power parameter as a function of the distance of the points from the imaged layer, wherein the laser-power is a decreasing function of the distance. FIG. 6G illustrates the implementation where this function is essentially a two-valued step-function. FIG. 6H illustrates the implementation where this function is a continuous function, its value decaying with the increasing distance from the imaged layer. In some implementations, it may be easier to control the laser power in the continuous manner of FIG. 6H.

The above-outlined implementations depend on the knowledge of the distance between the points of the scan-pattern and the imaged layer. Three stages are involved in determining this distance. First, the identity of the imaged layer is identified in the image 252 to determine the image 256 of the imaged layer. Then, the z-depth coordinate of the imaged layer is determined. Finally, the distance of the imaged layer and the points of the scan-pattern can be determined, for example, by taking the difference of the z-depth coordinates of the points of the scan-pattern and the imaged layer at the corresponding angular scanning coordinates, such as at the same angle.

Concerning the first step, the raw image 252 does not isolate or identify the imaged layer explicitly. Thus, establishing the identity of the imaged layer may necessitate an analysis of the image 252. As discussed earlier, this analysis of the image can be performed by the imaging system 122, the pattern generator 124, or the image analyzer 126, possibly assisted by an input from a system operator through the operator interface 128.

Figure 7:
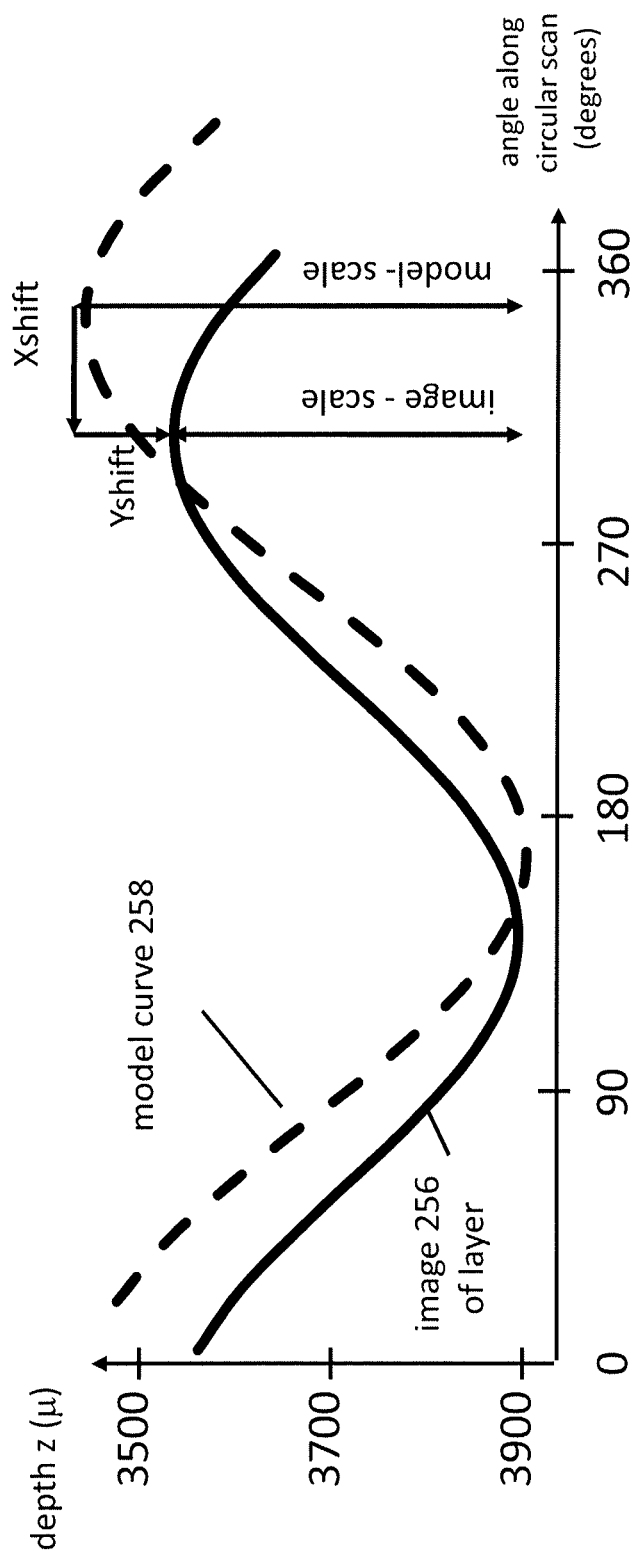
FIG. 7 illustrates a determination of the z-depth of the imaged layer by using a model curve.

FIG. 7 illustrates that the imaging system 122 can support the identification of the imaged layer and the determination of its z-depth coordinates in different ways. In some implementations the laser system 100 can include the operator interface 128 and the imaging system 122 can support the identification of the imaged layer using an input from an operator through the operator interface 128.

For example, on a graphical user interface, or GUI, the operator interface 128 can prompt the operator to fit a model curve 258 to the spots in the image 252 representing the imaged layer. Since in the case of a tilted ellipsoid-shaped lens the image 256 of the imaged layer is typically a sinusoidal curve, the operator interface 128 can display a generic sinusoidal curve 258 on the GUI and prompt the operator to fit this model curve 258 to the layer-spots in the image 252. Once the operator fitted the model curve 258 to the layer-spots in the image 252, the model curve 258 can serve as the image 256 of the imaged layer.

The operator can achieve this task through various approaches: by shifting the model curve 258 by an Xshift in the X direction (i.e. adjusting the angle along the circular scan) and by shifting the model curve 258 by a Yshift in the Y direction (i.e. adjusting the z-depth coordinate). In other implementations the operator can be prompted to adjust the scale of the model curve 258 to the scale of the sinusoidally located layer-spots in the image 252, i.e. to rescale the z-depth of the model curve 258 to fit the z-depth of the layer-spots. Many other fitting techniques can be implemented to achieve analogous functionalities.

The operator interface 128 can receive the input from the operator in many different ways, including through a keyboard, a touch-screen, a computer-communication channel, an external memory, a flash-drive, an internet connection, a speech-recognition apparatus or a wireless connection.

In other implementations, the determination of the identity and the z-depth of the imaged layer can be performed by the laser system 100 without the input of a surgeon or operator. In particular, the imaging system 122 can be configured to determine the identity and then the z-depth coordinate of the imaged layer by a processor or microcomputer performing a feature-recognition analysis of the image 252. For example, the imaging system 122 can determine the identity and coordinates of the imaged layer by locating local maxima of the gradient of the spot intensity. In other implementations, an edge-recognition algorithm can be used. In these implementations, the imaging system 122 can identify the manifold of the maximum-gradient points as the image 256 of the imaged layer without resorting to fitting a model curve 258. In some implementations, of course, the imaging system 122 can make use of a model curve 258 to identify the image 256 of the imaged layer.

In the above implementations, once the identity of the imaged layer has been determined in the image 252, the z-depth coordinates of the imaged layer can be determined in a straightforward manner, for example, by counting the pixels in the image 252, or using a reference or a look-up table.

For the image analysis, the imaging system 122 can utilize a result of a pre-surgery measurement, statistical data, video image data, ophthalmic coherence tomography image data, or a model-based computation during the determination of the z-depth.

Once the z-depth of the imaged layer has been determined, the imaging system 122 can forward the z-depth and the corresponding scanning coordinates of the imaged layer to the pattern generator 124 to carry out the last stage, the determination of the distance between the imaged layer and the points of the scan-pattern, generated by the pattern generator 124. This stage can be carried out, for example, by subtracting the z-depth coordinates of the points of the scan-pattern from the z-depth coordinates of the imaged layer that correspond to the same scanning variable, such as the same scanning angle.

Finally, having determined the distance of the points of the scan-pattern from the imaged layer, the pattern generator 124 can associate a laser-power parameter above a photodisruption threshold with those points that are closer to the imaged layer than a predetermined distance, and associate a laser-power parameter below a photodisruption threshold with those points that are farther from the imaged layer than the predetermined distance, as described in relation to FIGS. 6A-H.

In some implementations, the imaging system 122 only captures the image 252 but does not identify the imaged layer or determine its z-depth coordinates. In these embodiments, the imaging system 122 can simply forward the unprocessed image 252 to the pattern generator 124 without analyzing it. The pattern generator 124 can receive the image 252, identify the imaged layer and determine the z-depth coordinate of the imaged layer corresponding to a scanning coordinate along an image scan.

As above, in some implementations, the pattern generator 124 can determine the z-depth of the imaged layer by performing a feature-recognition analysis of the received image 252. In other implementations, the pattern generator 124 can receive an operator input through the operator interface 128 during the process of determining the z-depth of the imaged layer, as described before.

In these implementations, once the z-depth coordinates of the imaged layer have been determined, the pattern generator 124 can define a tracking band 257 as a manifold of the points of the scan-pattern that are within a predefined distance from the coordinates of the imaged layer. Then the pattern generator 124 can associate a laser-power parameter above a photodisruption threshold with points of the scan-pattern inside the tracking band 257, and a laser-power parameter below a photodisruption threshold with points of the scan-pattern outside the tracking band 257.

Yet other implementations of the laser controller 120 may include an image analyzer 126 that can determine the z-depth coordinate of the imaged layer corresponding to a scanning coordinate along an image-scan. As was illustrated in FIGS. 3B-D, the image analyzer 126 can be self-standing or at least partially integrated with the imaging system 122 or the pattern generator 124.

The image analyzer 126 can identify the imaged layer and determine the z-depth coordinate of the imaged layer by performing a feature-recognition analysis of the image 252. In other implementations, the image analyzer 126 can determine the z-depth coordinate by making use of an operator input through an operator-interface 128.

The operation of the laser system 100 can be demonstrated on the example of the capsulotomy procedure, where the imaged layer is the lens capsule 222 between the lens 220 and the aqueous anterior chamber 230. In this case, the scan-pattern corresponds to the cut-cylinder 260-$c$ intersecting the lens capsule 222 at the capsulotomy cut 250. The pattern generator 124 can associate a photodisruptive laser-power parameter with points inside a tracking band 257 related to the intersection 250 of the cut-cylinder 260-$c$ and the lens capsule 222, and a non-photodisruptive laser-power parameter with points outside the tracking band 257.

Figures 8A, 8B:
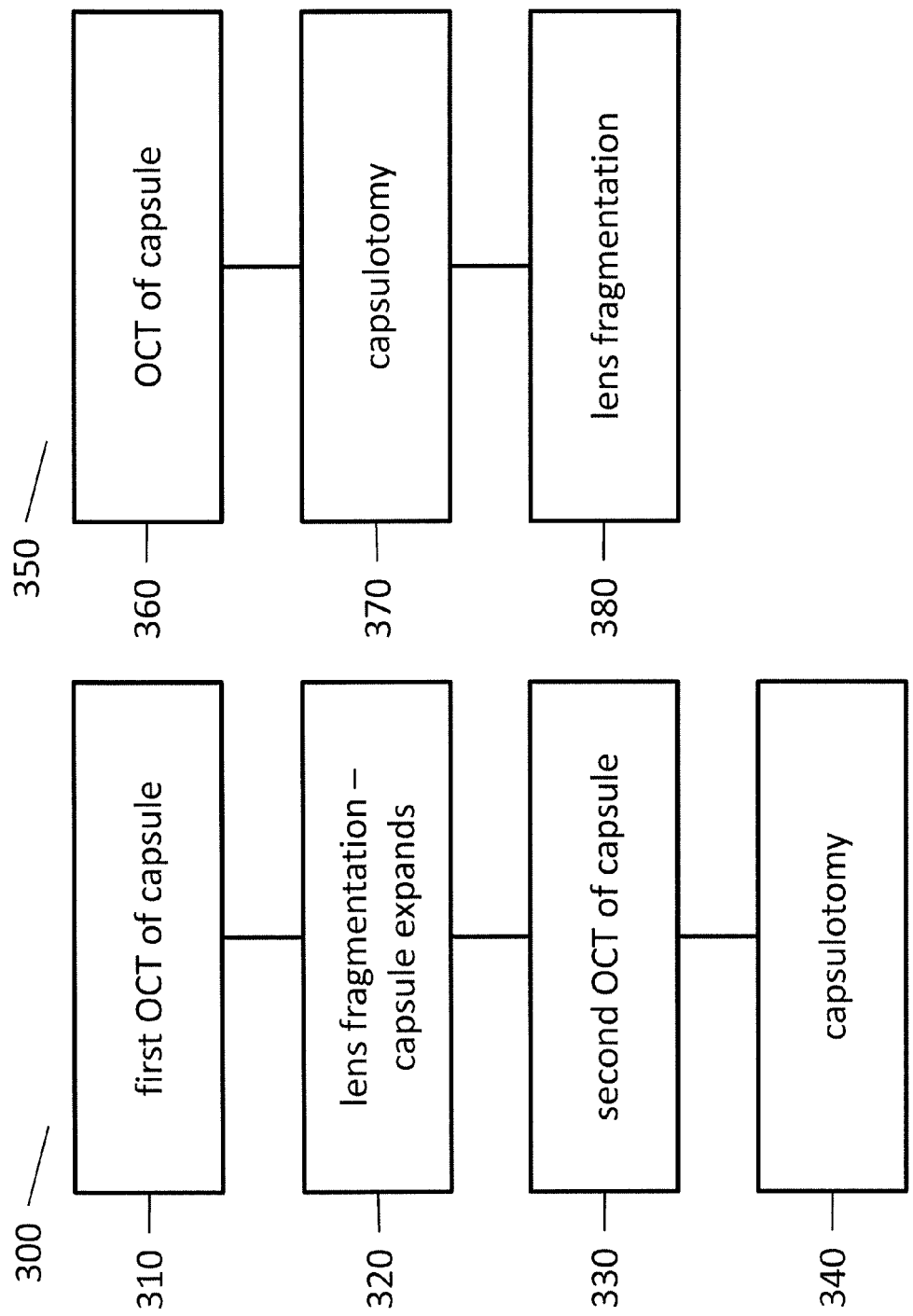
FIG. 8A-B illustrate methods of cataract surgery with the lens fragmentation and capsulotomy in different sequences.

FIG. 8A illustrates a first cataract procedure 300 performed without the benefits of the laser system 100. The cataract procedure 300 can be practiced when the capsulotomy generates an excessive number of bubbles as in FIGS. 4B-5B. To prevent excessive scattering by these capsulotomy bubbles, the lens fragmentation is performed prior to the capsulotomy. In detail, the cataract procedure 300 can include a first imaging 310 of the capsule 222, performed by an OCT procedure, followed by a lens fragmentation 320. During the lens fragmentation 320 the capsule 222 expands because of the large number of bubbles generated in the crystalline lens 220. The fragments of the lens 220 are removed through an opening, cut into the capsule 222 by a capsulotomy 340. However, since the capsule 222 has expanded during the lens fragmentation 320, the results of the first imaging 310 are not reliable anymore. Therefore, the capsulotomy 340 has to be preceded by a second imaging 330. The second imaging 330 can take up precious surgical time and increase the discomfort of the patient. Both of these factors can endanger the efficacy of the cataract procedure 300.

FIG. 8B illustrates a cataract procedure 350 with an embodiment of the laser system 100. Since the laser system 100 is capable of creating only a limited number of bubbles during the capsulotomy, the capsulotomy can be performed before the lens fragmentation. This change of sequence can reduce the surgical time to a considerable degree and thus increase the precision of the cataract procedure substantially.

In some detail, the cataract procedure 350 can include an imaging 360 of the capsule 222, e.g. by an OCT imaging system, followed by a capsulotomy 370, and completed by a lens fragmentation 380. Since the capsulotomy 370 does not deform the lens 220, there is no need for a second imaging, in contrast to the procedure 300.

Figure 9:
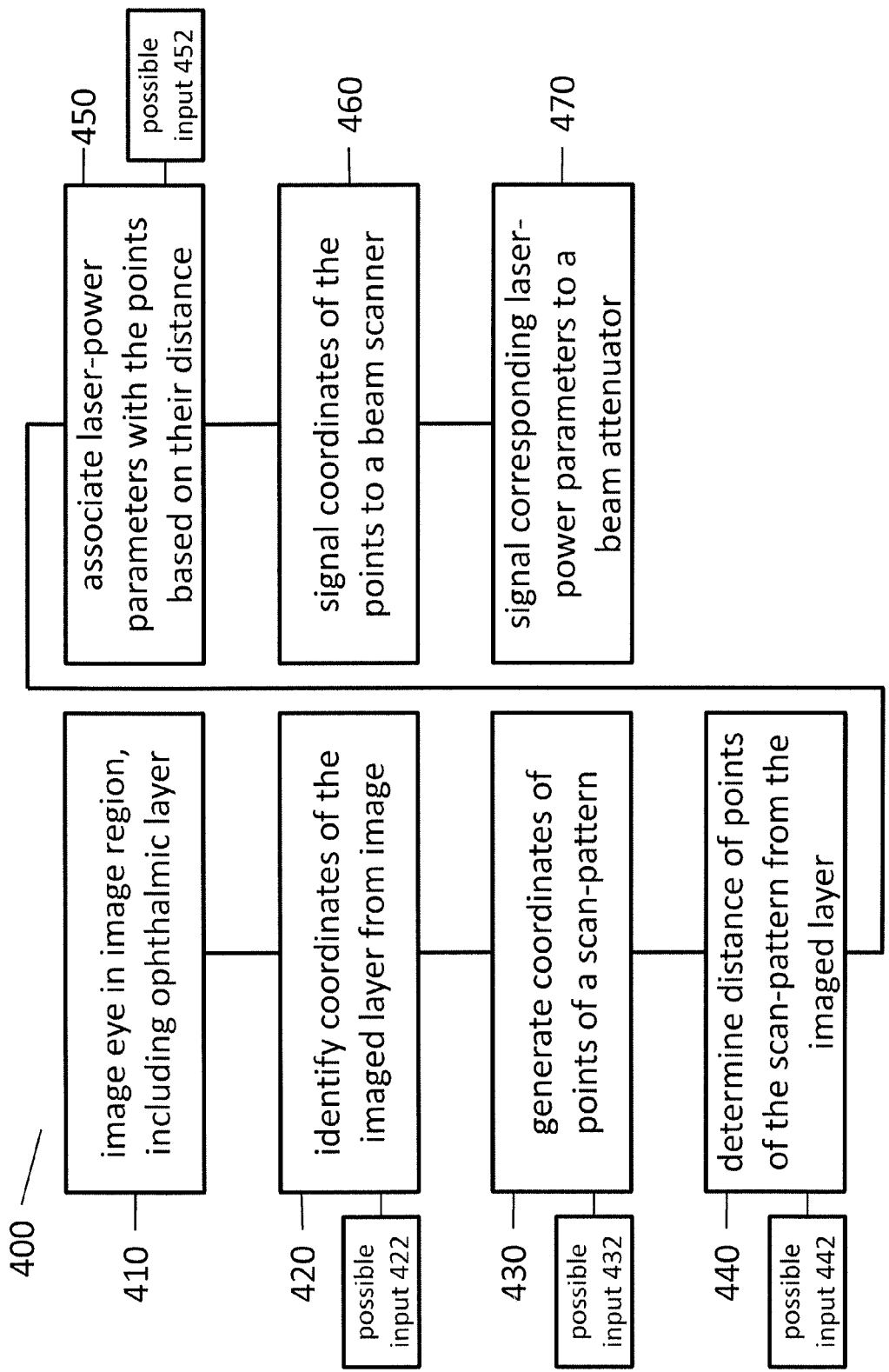
FIG. 9 illustrates a method of cataract surgery with an imaging-controlled laser system in detail.

FIG. 9 illustrates an imaging-controlled cataract method 400 in more detail. The method 400 can include an imaging 410 of an imaged ophthalmic layer in an imaged region of an eye, followed by an identifying 420 of the coordinates of the imaged layer from the image. These tasks can be performed, for example, by the imaging system 122 of the imaging-based laser-controller 120. The identifying 420 can include performing a feature-recognition analysis. In other cases, it can include receiving an operator-input through an operator interface 128. These tasks can be performed by the imaging system 122, the pattern generator 124 or the image analyzer 126.

Next, the method 400 can include a generating 430 of coordinates of points of a scan-pattern, and a determining 440 of a distance of the points of the scan-pattern from the imaged layer. These steps can be performed for example, by the pattern generator 124.

The method 400 can further include an associating 450 of laser-power parameters with the generated points based on their determined distance. The tasks 420 to 450 can include receiving possible inputs 422-452 from an operator of the laser system 100 through the operator interface 128.

The method can also include a signaling 460 of the generated coordinates of the points of the scan-pattern to the beam scanner 116 and a signaling 470 of the corresponding laser-power parameters to the beam attenuator 114.

Figure 10:
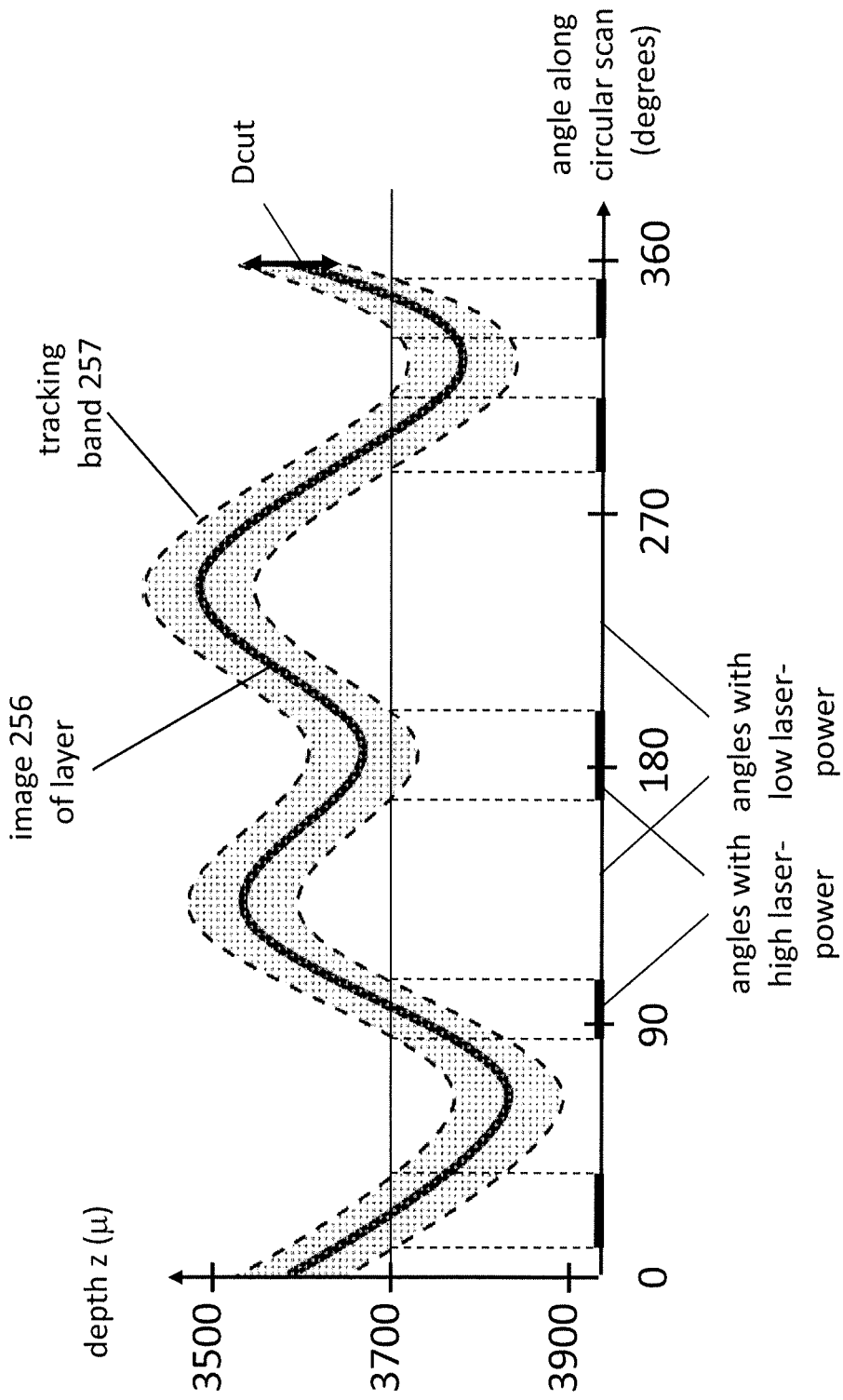
FIG. 10 illustrates a multi-extrema tracking-band laser scan-pattern after lens-fragmentation expanded the lens capsule in a non-uniform manner.

FIG. 10 illustrates the case of surgical relevance when the lens capsule 222 has an uneven shape. This situation can arise in different circumstances. For example, the docking of the patient interface 136 can cause considerable deformation of the anterior segment of the eye 1. Or an ophthalmic trauma or a prior lens fragmentation procedure can result in an uneven lens shape. In any of these circumstances, the laser system 100 can be capable of analyzing an image 256 of the imaged layer that exhibits more than two local extrema. Visibly, a simple sinusoidal model curve 258 is insufficient to identify the imaged layer and to determine its z-depth coordinate in this case. Therefore, embodiments of the imaging system 122, the pattern generator 124 or the image analyzer 126 can be capable of recognizing the imaged layer and determine its z-depth coordinate even in this more challenging case, for example, by using sophisticated feature-recognition software. Having determined and characterized the image 256 of the imaged layer can allow the pattern generator 124 to define the tracking band 257 to associate laser-power parameters with the spots of the scan-pattern accordingly.

FIGS. 11A-D illustrate that the imaging system 122 of the laser system 100 can image a region in the eye, the pattern generator 124 can generate coordinates of points of a scan-pattern for the beam scanner 116, and associate a laser-power parameter with the points of the scan-pattern depending on a distance of the points from a target-pattern.

Figures 11A, 11B:
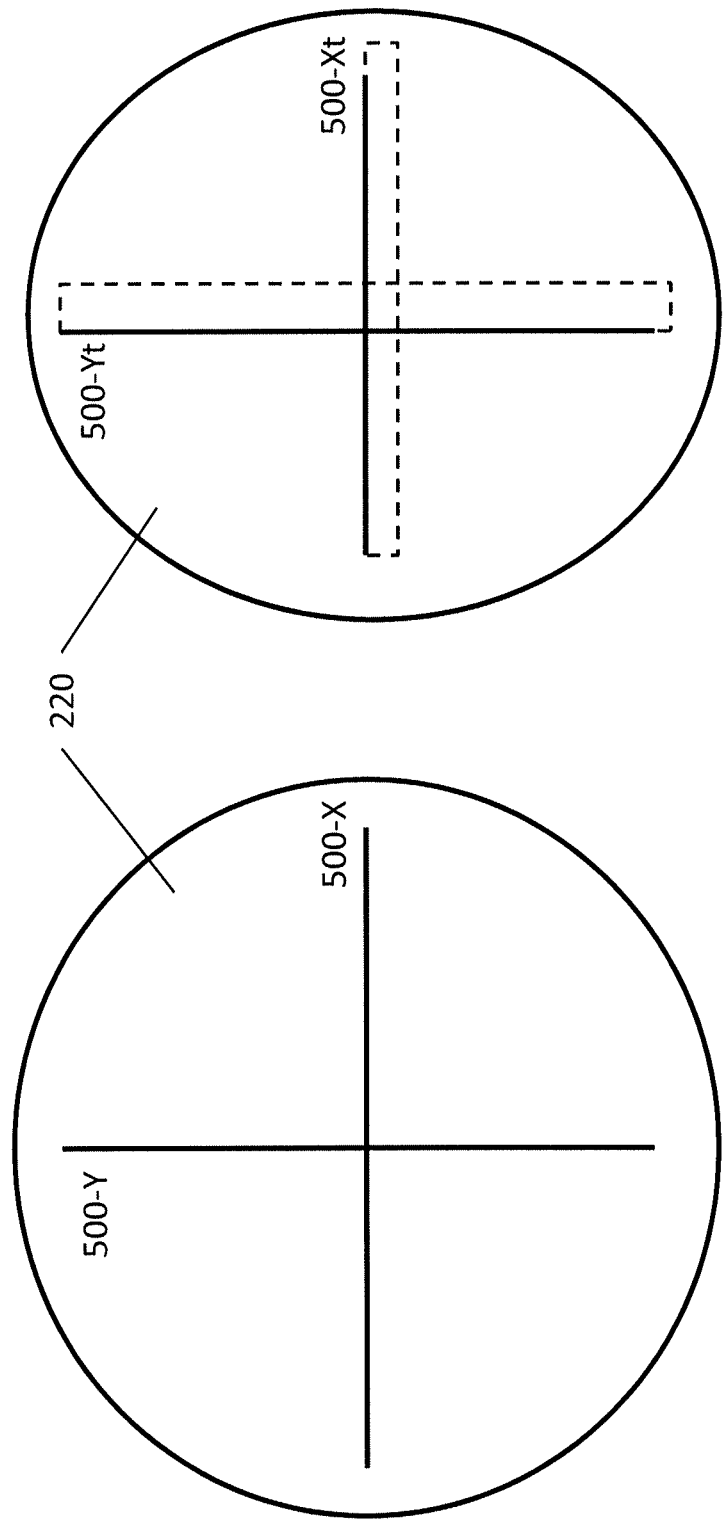
FIGS. 11A-D illustrate scan-patterns for tilted chop cuts.

An example for such a target pattern can be a chop pattern 500, including the chop-planes 500-X and 500-Y. Such chop patterns 500 can be used for lens fragmentation. FIG. 11A illustrates the case when the z-axis of the lens 220 is aligned with the z-axis of the laser system 100. In this case the chop-planes 500-X and 500-Y are also parallel to the z-axis of the laser system 100.

FIG. 11B illustrates that if the lens 220 is tilted relative to the z-axis of the laser system 100, as illustrated e.g. in FIG. 4B, then the chop planes 500-Xt and 500-Yt can be tilted as well. Since the scan-pattern often includes a first manifold of points at a first fixed z-depth, followed by a second manifold at a slightly lesser z-depth, the scan-pattern of tilted chop-planes with laser systems that cannot adjust the power of the laser pulses would create cuts into the capsular bag 222, leading to massive surgical complications.

In contrast, embodiments of the laser system 100 can associate laser-parameters depending on the distance of the points of the scan-pattern from the chop planes 500-Xt and 500-Yt.

Figure 11C:
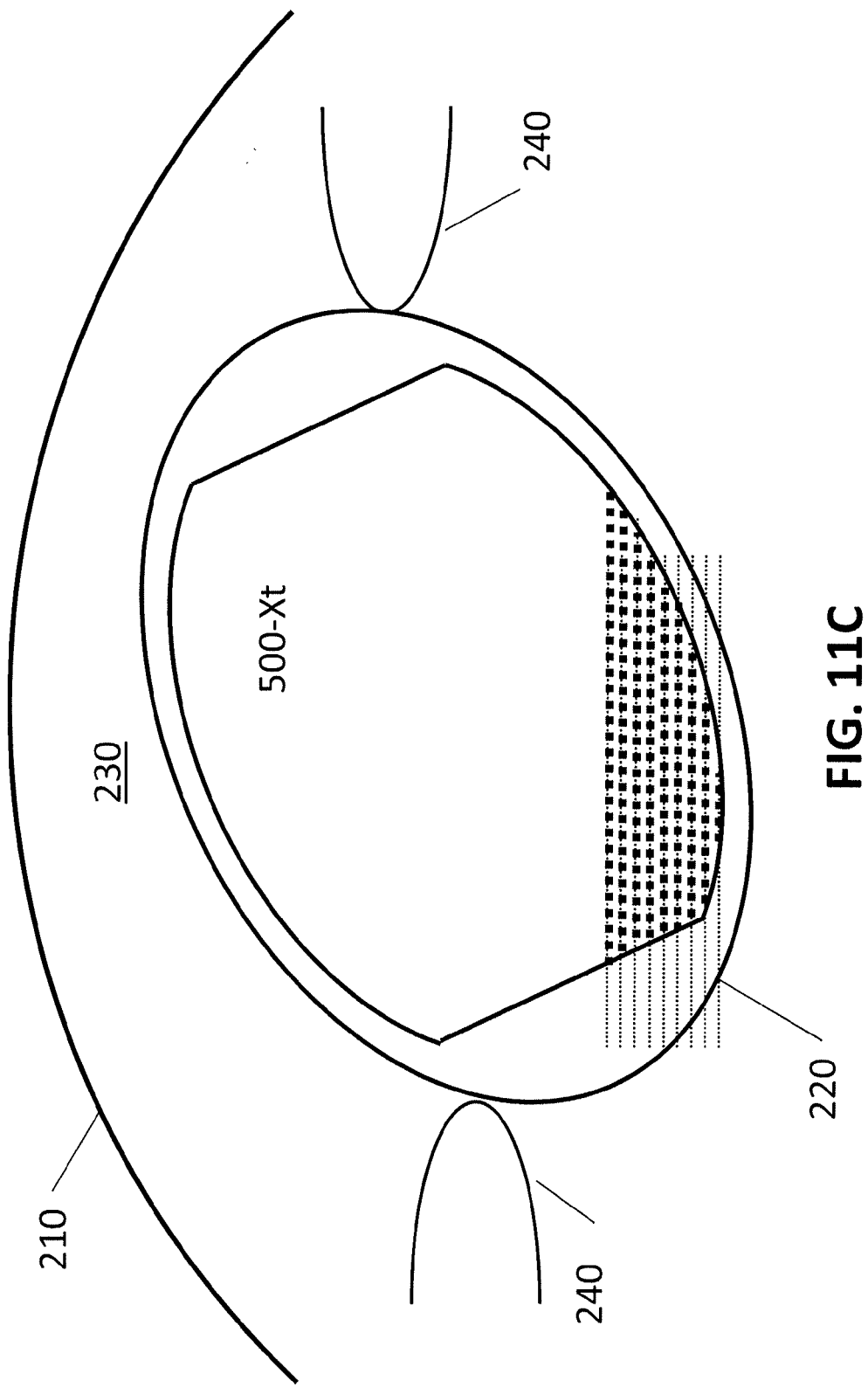
Figure 11D:
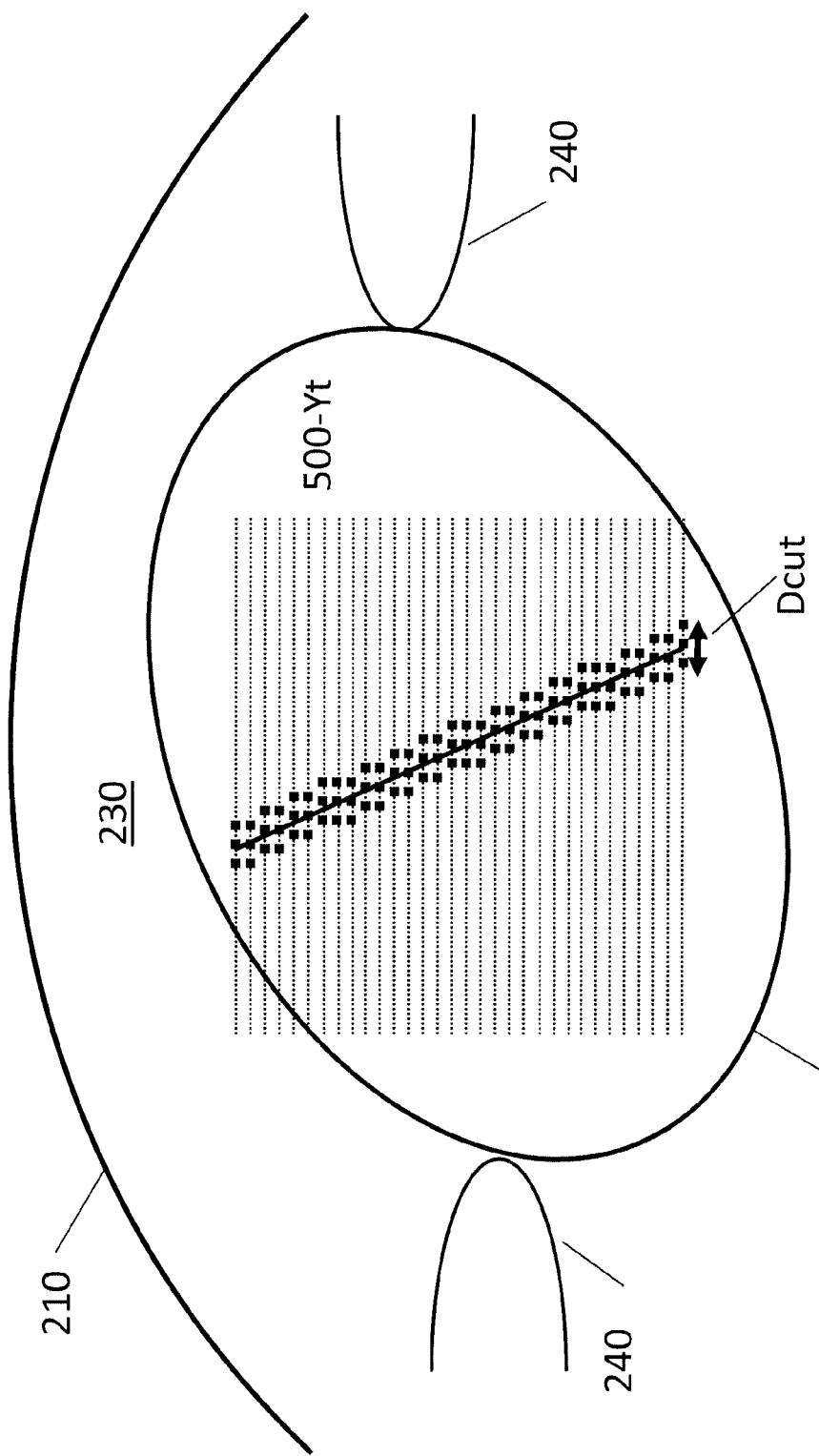

FIGS. 11C-D illustrate the points of the scan-pattern with low and high laser power, generated by the pattern generator 124 to form the tilted 500-Xt and 500-Yt chop planes. Visibly, creating cuts by adjusting the power of the laser pulses depending on their proximity to the target-pattern can avoid cutting into the capsular bag—a major surgical advantage.

FIG. 11D illustrates clearly that, as it was the case of the tracking band 257, a photodisruptive laser-power parameter can be associated with scan-points that are closer to the target-pattern 500-Xt and 500-Yt than a predetermined distance Dcut, and a non-photodisruptive laser-power parameter with the scan-points that are farther from the target-pattern than the predetermined distance Dcut.

In other implementations, the cutting surface can be a circular surface-segment, a spiral surface-segment, a corneal access cut and a limbal relaxing cut.

Figures 12A, 12B:
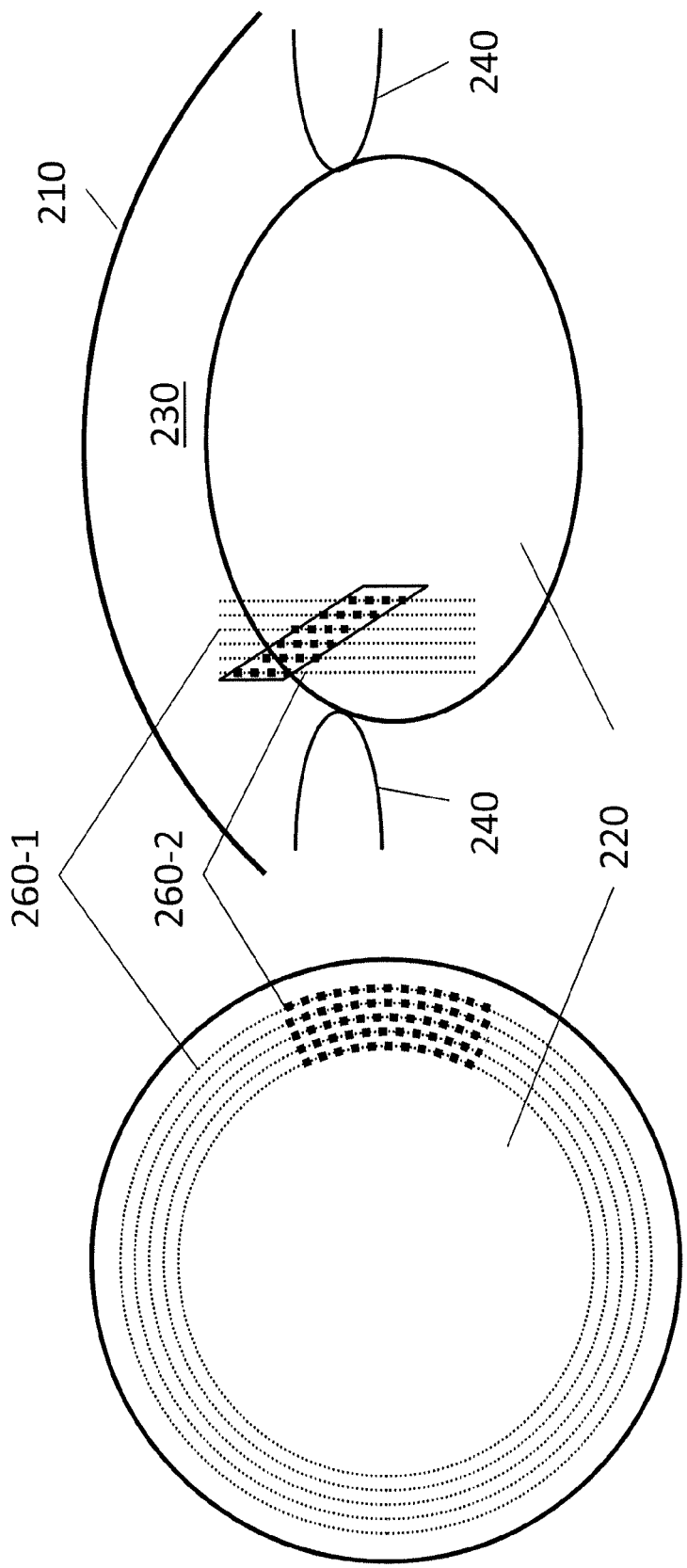
FIGS. 12A-B illustrate scan-patterns for tilted volume cuts.

FIGS. 12A-B illustrate that in some cases the target pattern 260-2 can be a target volume with an axis tilted relative to an optical axis of the laser system 100. Here, the scan pattern includes cylindrical patterns 260-1, and the laser-power parameter of the points of this scan-pattern is adjusted to form a tilted volume cut 260-2. Such a utility can be useful for correcting a refractive property of the lens 220, for example.

In some implementations, the pattern generator 124 can be configured to associate the laser-power parameters with the points of the scan-pattern depending additionally on a distance of the points from an ophthalmic layer, imaged by the imaging system 122.

While this specification contains many specifics, these should not be construed as limitations on the scope of the invention or of what can be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features can be described above as acting in certain combinations and even initially claimed as such, one or more features from a claimed combination can in some cases be excised from the combination, and the claimed combination can be directed to a subcombination or variation of a subcombination.

The invention claimed is:

1. An imaging-based laser system, comprising:
   a laser-beam system, including
      a laser engine, configured to generate a beam of laser pulses,
      a beam attenuator, configured to modify a laser-power parameter of the laser pulses, wherein the laser-power parameter is one of a pulse energy, a pulse power, a pulse length and a pulse repetition rate, and
      a beam scanner, configured to scan the beam to points of a cylindrical scan-pattern in an eye; and
   an imaging-based laser-controller, configured to:
      image a layer in the eye that is tilted relative to an optical axis of the laser system,
      determine z-depths of a sequence of points in the cylindrical scan-pattern that correspond to the imaged layer in the eye,
      generate a tracking band within the cylindrical scan pattern defining a cut to be made in the eye, wherein a lower boundary of the tracking band has a non-uniform z-depth that varies according to the determined z-depths of the sequence of points corresponding to the imaged layer,
      cause the beam scanner to scan the beam of laser pulses to the points of the cylindrical scan-pattern, and
      cause the beam attenuator to control the laser-power parameter of the laser pulses such that a laser power parameter of laser pulses in the tracking band is above a photo-disruption threshold, and a laser power parameter of laser pulses outside the tracking band is below the photo-disruption threshold.

2. The laser system of claim 1, the beam attenuator comprising at least one of:

a Pockels cell, a polarizer-assembly, a mechanical shutter, an electro-mechanical shutter, and an energy wheel.

3. The laser system of claim 1, wherein:
the beam attenuator is disposed between the laser engine and the beam scanner in a path of the beam.

4. The laser system of claim 1, wherein:
the beam attenuator is disposed after the beam scanner in a path of the beam.

5. The laser system of claim 1, wherein:
the beam attenuator is part of the laser engine.

6. The laser system of claim 1, wherein:
the beam attenuator and the beam scanner are at least partially integrated.

7. The laser system of claim 1, the laser-controller comprising:
an imaging system, configured to image the imaged layer in the eye; and
a pattern generator, configured to:
generate coordinates of each point within the cylindrical scan-pattern,
associate a particular laser-power parameter with each point in the cylindrical scan pattern based on the tracking band, and
signal the generated coordinates of each point to the beam scanner, and
signal the particular laser-power parameter of each point to the beam attenuator.

8. The laser system of claim 7, the imaging system comprising:
at least one of an ophthalmic coherence tomography system, a Scheimpflug imaging system, a scanning imaging system, a single shot imaging system, an ultrasound imaging system, and a video imaging system.

9. The laser system of claim 7, wherein:
the imaging system is configured to image the imaged layer in an image region, wherein the image region
is based on one of a loop, an arc, a line, and a two-dimensional pattern transverse to an axis of the imaging system, and
extends to an image depth along the axis of the imaging system.

10. The laser system of claim 7, wherein:
the imaging system is configured to support a determination of a z-depth coordinate of the imaged layer corresponding to a scanning coordinate along an image-scan.

11. The laser system of claim 10, wherein:
the laser system comprises an operator interface; and
the imaging system is configured to support the determination of the z depth coordinate of the imaged layer using an input from an operator through the operator interface.

12. The laser system of claim 11, wherein:
the operator interface is configured to assist the operator to fit a model curve to the image of the imaged layer.

13. The laser system of claim 11, wherein:
the operator interface is capable of receiving the operator-input from at least one of a keyboard, a touch-screen, a computer-communication channel, an external memory, a flash-drive, an internet connection, a speech-recognition apparatus and a wireless connection.

14. The laser system of claim 10, wherein:
the imaging system is configured to determine the z-depth coordinate of the imaged layer by performing a feature-recognition analysis of the image of the imaged layer.

15. The laser system of claim 14, wherein:
the imaging system is configured to utilize at least one of a result of a pre-surgery measurement, statistical data, video image data, ophthalmic coherence tomography image data,
and a model-based computation during the determination of the z-depth.

16. The laser system of claim 10, wherein:
the imaging system is configured to forward the z-depth and scanning coordinates of the imaged layer to the pattern generator; and
the pattern generator is configured
to determine the distance of the points of the scan-pattern from the imaged layer based on the forwarded coordinates of the imaged layer and the generated coordinates of the points,
to associate a first laser-power parameter above a photodisruption threshold with a first set of points closer to the imaged layer than a predetermined distance, and
to associate a second laser-power parameter below a photodisruption threshold with a second set of points farther from the imaged layer than the predetermined distance.

17. The laser system of claim 10, wherein:
the imaging system is configured to forward the z-depth and scanning coordinates of the imaged layer to the pattern generator; and
the pattern generator is configured
to determine the distance of the points of the scan-pattern from the imaged layer based on the forwarded coordinates of the imaged layer and the generated coordinates of the points, and
to associate with the coordinates of the points a laser-power parameter that is a decreasing function of the distance of the points from the imaged layer.

18. The laser system of claim 7, wherein:
the imaging system is configured to forward the image of the imaged layer to the pattern generator; and
the pattern generator is configured
to receive the image from the imaging system, and
to determine a z-depth coordinate of the imaged layer corresponding to a scanning coordinate along an image scan.

19. The laser system of claim 18, wherein:
the pattern generator is configured to determine the z-depth of the imaged layer in part by performing a feature-recognition analysis of the received image of the imaged layer.

20. The laser system of claim 18, wherein:
the pattern generator is configured to receive an operator input through an operator interface during the process of determining the z-depth of the imaged layer.

21. The laser system of claim 20, wherein:
the operator interface is capable of receiving the operator-input from at least one of a keyboard, a touch-screen, a computer-communication channel, an external memory, a flash-drive, an internet connection, a speech-recognition apparatus and a wireless connection.

22. The laser system of claim 18, wherein:
the pattern generator is configured to:
generate the tracking band as a manifold of points within a predefined distance from the coordinates of the imaged layer;

associate a laser-power parameter above a photodisruption threshold with points of the scan-pattern inside the tracking band, and to associate a laser-power parameter below a photodisruption threshold with points of the scan-pattern outside the tracking band.

23. The laser system of claim 7, the laser controller comprising:

an image analyzer, configured to determine a z-depth coordinate of the imaged layer corresponding to a scanning coordinate along an image-scan.

24. The laser system of claim 23, wherein:
the image analyzer is configured to determine the z-depth coordinate of the imaged layer by performing a feature-recognition analysis of the image of the imaged layer.

25. The laser system of claim 23, wherein:
the image analyzer is configured to determine the z-depth coordinate of the imaged layer by receiving an operator input through an operator-interface.

26. The laser system of claim 23, wherein:
the image analyzer is at least partially integrated with one of the imaging system and the pattern generator.

27. The laser system of claim 1, wherein:
the imaged layer is a lens capsule between a lens of an eye and an aqueous anterior chamber of the eye;
the scan-pattern corresponds to a cylindrical capsulotomy cut intersecting the lens capsule; and
the imaging-based laser controller is configured to:
associate a photodisruptive laser-power parameter with points inside a tracking band related to the intersection of the cylindrical capsulotomy cut and the lens capsule, and
associate a non-photodisruptive laser-power parameter with points outside the tracking band.

28. The laser system of claim 27, wherein:
the laser system is configured to perform a capsulotomy before a lens fragmentation during a cataract procedure.

29. The laser system of claim 27, wherein:
the imaging-based laser controller is configured to to analyze an image of the capsule boundary layer with more than two local extrema by at least one of a pattern generator and an image analyzer.

* * * * *